United States Patent [19]
Krämer et al.

[11] Patent Number: 4,826,857
[45] Date of Patent: May 2, 1989

[54] FUNGICIDAL AGENTS

[75] Inventors: Wolfgang Krämer, Wuppertal; Joachim Weissmuller, Monheim; Wolf Reiser, Wuppertal; Dieter Berg, Wuppertal; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 176,479

[22] Filed: Apr. 1, 1988

Related U.S. Application Data

[62] Division of Ser. No. 55,487, May 28, 1987, Pat. No. 4,755,521, which is a division of Ser. No. 735,498, May 17, 1985, Pat. No. 4,713,379.

[30] Foreign Application Priority Data

Jun. 5, 1984 [DE] Fed. Rep. of Germany ....... 3420828

[51] Int. Cl.$^4$ ..................... A01N 43/40; A01N 43/64
[52] U.S. Cl. ..................... 514/326; 514/383
[58] Field of Search ................. 514/326, 383

[56] References Cited

U.S. PATENT DOCUMENTS 4,503,059 3/1985 Kramer et al. ..................... 514/212

OTHER PUBLICATIONS

Fuchs et al.; Fungicide Resistance in Crop Protection Center for Agriculture Publishing and Documentation, 1982 pp. 71–86.
Chemical Abstracts, vol. 78, 1973, p. 67, Abstract 144283c.

Primary Examiner—Allen J. Robinson
Attorney, Agent, or Firm—Sprung Horn Kramer & Woods

[57] ABSTRACT

A synergistic fungicidal composition comprising a fungicidally effective amount of at least one amino compound of the formula

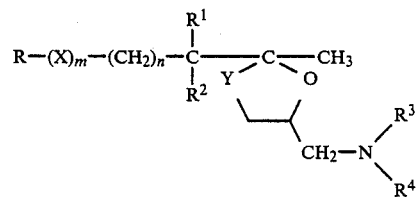

in which
R represents optionally substituted cycloalkyl or optionally substituted aryl,
$R^1$ represents hydrogen or alkyl,
$R^2$ represents alkyl,
$R^3$ represents alkyl and
$R^4$ represents alkyl, alkenyl or alkinyl, or
$R^3$ and $R^4$, together with the nitrogen atom to which they are bonded, represent an optionally substituted saturated heterocyclic radical, which can contain further hetero-atoms,
X represents oxygen or sulphur,
Y represents oxygen, sulphur or the methylene group,
m represents 0 or 1 and
n represents 0 or 1, or an addition product thereof with an acid, metal salt or quaternizing agent, and at least one member selected from the group consisting of several individually known fungicides.

8 Claims, No Drawings

FUNGICIDAL AGENTS

This is a division of application Ser. No. 055,487, filed May 28, 1987, now U.S. Pat. No. 4,755,521, which is a division of application Ser. No. 735,498, filed May 17, 1985, now U.S. Pat. No. 4,713,379.

The invention relates to new fungicidal synergistic active compound combinations of particular amino compounds, some of which are known, and other known fungicidal active compounds.

It is already known that certain amino compounds, such as, for example, the amino-ketals 4-(3,5-dimethyl-piperidin-1-yl-methyl)-2-[1-(4-fluorophenyl)-2-methyl-prop-2-yl]-2-methyl-1,3-dioxolane or 2-[1-(4-fluorophenyl)-2-methyl-prop-2-yl]-2-methyl-4-(3-methyl-piperidin-1-yl-methyl)-1,3-dioxolane, have fungicidal properties (compare, for example, DE-OS (German published Specification) No. 3,305,769).

The following groups of fungicidal active compounds are also known:

(A) Azoles, such as, for example, 1-(4-chlorophenoxy)-3,3-dimethyl-1-(1,2,4-triazol-1-yl)-butan-2-one (compare, for example, R. Wegler "Chemie der Pflanzenschutz-und Schädlingsbekämpfungsmittel" ("Chemistry of Plant Protection Agents and Agents for combating pests"), Volume 4, pages 206 to 208, Springer Verlag, Berlin, Heidelberg, New York 1977), (B) Pyrimidine derivatives, such as, for example, (2,4-dichlorophenyl)-(phenyl)-(pyrimidin-5-yl)-carbinol or (2-chlorophenyl)-(4-chlorophenyl)-(pyrimidin-5-yl)-carbinol (compare, for example, R. Wegler "Chemie der Pflanzenschutz-und Schädlingsbekämpfungsmittel" ("Chemistry of Plant Protection Agents and Agents for combating pests"), Volume 4, pages 213/214; Springer Verlag Berlin, Heidelberg, New York 1977), (C) Pyridine derivatives, such as, for example, S-(n-butyl) S-(4-t-butyl-phenylmethyl) N-(3-pyridyl)-iminodithiocarbonate (compare, for example, Japanese patent application Ja No. 43,334/72), and (D) Morpholino compounds, such as, for example, cis-2,6-dimethyl-4-[3-(4-t-butylphenyl)-2-methyl-prop-1-yl]morpholine (compare, for example, DE-OS (German published specification) No. 2,656,747).

Synergistic mixtures of azoles and other fungicides which have a considerably higher action than that expected from the actions of the individual components are also known (compare, for example, DE-OS (German published specification) No. 2,552,967 corresponding to U.S. Pat. No. Re. 31,693).

The activity of the known fungicidal active compounds as individual compounds and also that of the known synergistic active compound combinations are, however, not always completely satisfactory in all fields of application, especially when low amounts and concentrations are used.

It has now been found, surprisingly, that the new active compound combinations of particular amino compounds, some of which are known, of the formula (I)

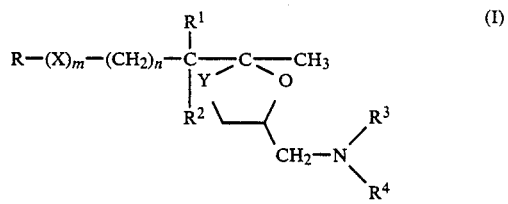

in which
R represents optionally substituted cycloalkyl or optionally substituted aryl,
$R^1$ represents hydrogen or alkyl,
$R^2$ represents alkyl,
$R^3$ represents alkyl and
$R^4$ represents alkyl, alkenyl or alkinyl, or
$R^3$ and $R^4$, together with the nitrogen atom to which they are bonded, represent an optionally substituted saturated heterocyclic radical, which can contain further hetero-atoms,
X represents oxygen or sulphur,
Y represents oxygen, sulphur or the methylene group,
m represents 0 or 1 and
n represents 0 or 1,
or acid addition salts, metal salt complexes or quaternization products thereof which are tolerated by plants, on the one hand, and, on the other hand, known fungicidal active compounds either from the group ($A_1$) with the formula (IIa)

in which
$R^5$ represents alkyl, alkenyl, alkinyl, cycloalkyl, alkylcarbonyl, optionally substituted phenyl, optionally substituted phenylcarbonyl, an optionally substituted heterocyclic radical, the cyano group, an ester grouping or an acid amide radical,
$R^6$ represents alkyl, cycloalkyl or optionally substituted phenyl,
$R^7$ represents optionally substituted phenyl and
Z represents nitrogen or the CH group,
or acid addition salts or metal salt complexes thereof which are tolerated by plants, and/or from the group ($A_2$) with the formula (IIb)

in which
$R^8$ represents hydrogen or in each case optionally substituted alkyl, alkenyl, alkinyl, cycloalkyl, aryl, aryloxy or heteroaryloxy,
$R^9$ represents in each case optionally substituted alkylcarbonyl or arylcarbonyl, or represents a functional derivative of these groups, such as oxime, hydrazone or ketal, or furthermore represents a carboxyl group or a functional derivative thereof, such as ester or amide, or furthermore represents a radical

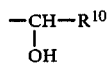

or a functional derivative thereof, such as ester or ether,
wherein
$R^{10}$ represents in each case optionally substituted alkyl or aryl, and
Z has the abovementioned meaning,
or acid addition salts or metal salt complexes thereof which are tolerated by plants, and/or from the group ($A_3$) with the formula (IIc)

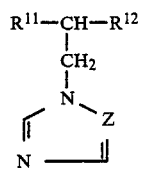

in which
$R^{11}$ represents in each case optionally substituted aryl or aryloxy and
$R^{12}$ represents alkyl or a radical $-S(O)_p-R^8$,
wherein
p represents 0, 1 or 2 and
$R^8$ has the abovementioned meaning, or
$R^{12}$ also represents in each case optionally substituted alkylcarbonyl or arylcarbonyl or a functional derivative of these groups, such as oxime, hydrazone or ketal, or represents a radical

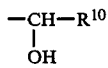

or a functional derivative thereof, such as ester or ether,
wherein $R^{10}$ and Z have the abovementioned meaning,
or acid addition salts or metal salt complexes thereof which are tolerated by plants, and/or from the group ($A_4$) with the formula (IId)

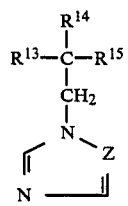

in which
$R^{13}$ represents in each case optionally substituted alkyl, alkenyl, alkinyl, cycloalkyl, heterocyclyl, aryl or heteroaryl,
$R^{14}$ represents in each case optionally substituted alkyl, alkenyl, alkinyl, cycloalkyl or aryl,
$R^{15}$ represents chlorine, cyano or a radical $-OR^{16}$,
wherein
$R^{16}$ represents hydrogen or in each case optionally substituted alkyl, alkenyl, alkinyl or acyl, and
Z has the abovementioned meaning,
or acid addition salts or metal salt complexes thereof which are tolerated by plants, and/or from the group ($A_5$) with the formula (IIe)

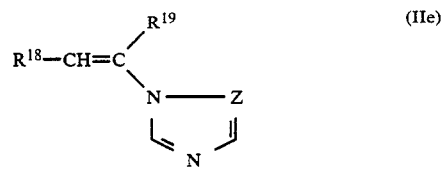

in which
$R^{18}$ represents in each case optionally substituted alkyl, cycloalkyl or aryl,
$R^{19}$ represents in each case optionally substituted alkylcarbonyl or arylcarbonyl or a functional derivative of these groups, such as oxime, hydrazone or ketal, or represents a radical

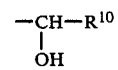

or a functional derivative thereof, such as ester or ether,
wherein $R^{10}$ and Z have the abovementioned meaning,
or acid addition salts or metal salt complexes thereof which are tolerated by plants, and/or from the group ($A_6$) with the formula (IIf)

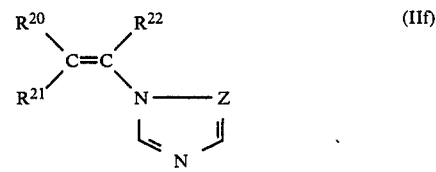

in which
$R^{20}$ represents alkyl, optionally substituted phenyl or optionally substituted phenoxy,
$R^{21}$ represents in each case optionally substituted alkylcarbonyl or arylcarbonyl or a functional derivative of these groups, such as oxime, hydrazone or ketal, or represents a radical

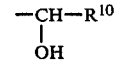

or a functional derivative thereof, such as ester, ether or trialkylsilyl ether,
$R^{22}$ represents hydrogen or in each case optionally substituted aryl or aryloxy and
$R^{10}$ and Z have the abovementioned meaning,
or acid addition salts or metal salt complexes thereof which are tolerated by plants, and/or from the group ($A_7$) with the formula (IIg)

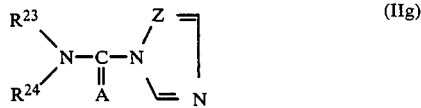

in which
$R^{23}$ represents alkyl, $R^{24}$ represents in each case optionally substituted alkyl, alkenyl, alkinyl, cycloalkyl or aryl, A represents oxygen or sulphur and z has the abovementioned meaning, or acid addition salts or metal salt complexes thereof which are tolerated by plants, and/or from the group ($A_8$) with the formula (IIh)

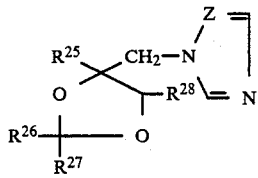

in which $R^{25}$ represents optionally substituted aryl, $R^{26}$ and $R^{27}$ in each case independently of one another represent hydrogen, alkyl or aryl, or together represent a divalent alkylene radical, $R^{28}$ represents hydrogen or alkyl and Z has the abovementioned meaning, or acid addition salts or metal salt complexes thereof which are tolerated by plants, and/or from the group (B) with the formula (III)

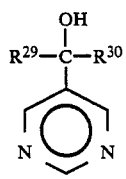

in which $R^{29}$ represents alkyl, cycloalkyl or optionally substituted aryl and $R^{30}$ represents in each case optionally substituted aryl, aralkyl or aryloxyalkyl, or acid addition salts thereof which are tolerated by plants, and/or from the group (C) with the formula (IV)

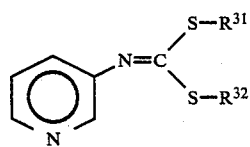

in which $R^{31}$ and $R^{32}$ independently of one another represent alkyl or optionally substituted aralkyl, or acid addition salts thereof which are tolerated by plants, and/or from the group (D) with the formula (V)

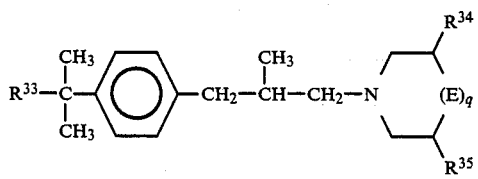

in which $R^{33}$ represents alkyl, cycloalkyl or halogenoalkyl, $R^{34}$ and $R^{35}$ independently of one another represent hydrogen, alkyl, hydroxyalkyl, hydroxyl or aryl, E represents oxygen, sulphur, divalent alkylene or the >N—$R^{36}$ group, wherein $R^{36}$ represents hydrogen or alkyl, and q represents 0 or 1, or acid addition salts thereof which are tolerated by plants—all the geometric and optical isomers of the compounds of the formulae (I) to (V) being included—have a particularly high fungicidal activity.

Surprisingly, the fungicidal action of the active compound combinations according to the invention of the amino compounds, some of which are known, of the formula (I), on the one hand, and azole derivatives of the formulae (IIa-h) and/or pyrimidine derivatives of the formula (III) and/or pyridine derivatives of the formula (IV) and/or amino compounds of the formula (V), on the other hand, is higher than the action of the individual components and also higher than the sum of the actions of the individual components (synergistic effect).

The active compound combinations according to the invention thus represent an enrichment of the art.

Formula (I) provides a general definition of the particular amino compounds, some of which are known, which are to be used for the active compound combinations according to the invention. Preferred compounds of the formula (I) are those in which R represents phenyl or cyclohexyl which is optionally monosubstituted or polysubstituted by identical or different substituents, possible substituents being: halogen and in each case straight-chain or branched alkyl, alkoxy, alkylthio, halogenoalkyl, halogenoalkoxy or halogenoalkylthio with in each case 1 to 4 carbon atoms and, where appropriate, 1 to 9 identical or different halogen atoms, $R^1$ represents hydrogen or straight-chain or branched alkyl with 1 to 4 carbon atoms, $R^2$ represents straight-chain or branched alkyl with 1 to 4 carbon atoms, $R^3$ represents straight-chain or branched alkyl with 1 to 6 carbon atoms and $R^4$ represents in each case straight-chain or branched alkyl, alkenyl or alkinyl with in each case up to 8 carbon atoms, or $R^3$ and $R^4$, together with the nitrogen atom to which they are bonded, represent a saturated heterocyclic radical which as 5 to 7 ring members and 1 or 2 hetero-atoms and is optionally mono-substituted or polysubstituted by identical or different substituents, possible hetero-atoms being nitrogen and oxygen and possible substituents being: straight-chain or branched alkyl with 1 to 4 carbon atoms, hydroxymethyl and derivatives thereof, such as ethers and esters, and straight-chain or branched alkoxycarbonyl with 1 to 4 carbon atoms, X represents oxygen or sulphur, Y represents oxygen, sulphur or the methylene group, m represents 0 or 1 and n represents 0 or 1, and acid addition salts, metal salt complexes and quaternization products thereof which are tolerated by plants.

Particularly preferred components of the mixture are amino compounds of the formula (I)

in which

R represents phenyl which is optionally mono-, di- or tri-substituted by identical or different substituents, possible substituents being: fluorine, chlorine, bromine, methyl, ethyl, n- and i-propyl, n-, i-, s- and t-butyl, methoxy, ethoxy, n- and i-propoxy, methylthio, trifluoromethyl, trifluoromethoxy and trifluoromethylthio, or represents cyclohexyl which is optionally mono-, di-, tri-, tetra- or penta-substituted by identical or different substituents, possible substituents being: methyl, ethyl and n- or i-propyl, $R^1$ represents hydrogen or methyl, $R^2$ represents methyl or ethyl, $R^3$ represents methyl and $R^4$ represents methyl, ethyl, n- or i-propyl, n- or i-butyl, n- or i-pentyl, n- or i-hexyl, allyl, butenyl, n- or i-pentenyl, n- or i-hexenyl, propargyl, butinyl, n- or i-pentinyl or n- or i-hexinyl, or $R^3$ and $R^4$, together with the nitrogen atom to which they are bonded, represent a heterocyclic radical of the formula

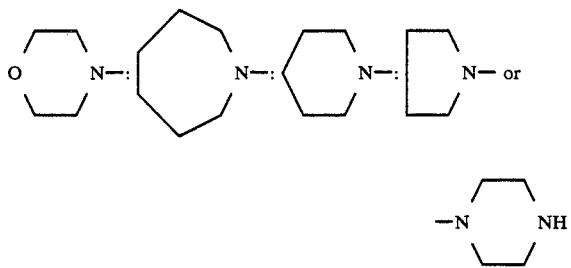

which is optionally mono-, di-, tri- or tetra-substituted by identical or different substituents, possible substituents being: methyl, ethyl, phenyl, hydroxymethyl, methoxymethyl, ethoxymethyl, acyloxymethyl, methoxycarbonyl or ethoxycarbonyl, X represents oxygen or sulphur, Y represents oxygen, sulphur or the methylene group, m represents 0 or 1 and n represents 0 or 1, and acid addition salts, metal salt complexes and quaternization products thereof which are tolerated by plants.

Some of the compounds of the formula (I) are disclosed in European patent application No. 97,822. Others are disclosed in German patent application No. 33 28 151 corresponding to U.S. application Ser. No. 630,487 filed July 13, 1984, now pending, German patent application No. 33 24 769 corresponding to U.S. application Ser. No. 624,889 filed June 27, 1984, now pending, and German patent application No. 34 14 996.

They are obtained, for example, by a process in which compounds of the formula (VI)

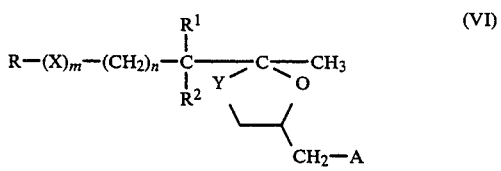

in which

R, $R^1$, $R^2$, X, Y, m and n have the abovementioned meaning and

A represents an electron-withdrawing leaving group, in particular chlorine or bromine, methanesulphonyloxy or p-toluenesulphonyloxy, are reacted with amines of the formula (VII)

in which $R^3$ and $R^4$ have the abovementioned meaning, if appropriate in the presence of a diluent, such as, for example, ethanol, if appropriate in the presence of an acid-binding agent, such as, for example, potassium carbonate, and if appropriate in the presence of a catalyst, such as, for example, potassium iodide, at temperatures between 50° C. and 250° C.

The following acids can preferably be used to prepare acid addition salts of the compounds of the formula (I) which are tolerated by plants: hydrogen halide acids, such as, for example, hydrochloric acid and hydrobromic acid, in particular hydrochloric acid, and furthermore phosphoric acid, nitric acid, sulphuric acid, mono-, bi- and tri-functional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and they can be isolated in a known manner, for example by filtration, and, if appropriate, purified by washing with an inert organic solvent.

Salts of metals of main groups II to IV and of subgroups I and II and IV to VIII can preferably be used to prepare metal salt complexes of the compounds of the formula (I), examples of metals which may be mentioned being copper, zinc, manganese, magnesium, tin, iron and nickel.

Possible anions of salts are those which, preferably, are derived from the following acids: hydrogen halide acids, such as, for example, hydrochloric acid and hydrobromic acid, and furthermore phosphoric acid, nitric acid and sulphuric acid.

The metal salt complexes of compounds of the formula (I) can be obtained in a simple manner by customary processes, thus, for example, by dissolving the metal salt in alcohol, for example ethanol, and adding the solution to the compound of the formula (I). The metal salt complexes can be purified in a known manner, for example by filtration, isolation and, if appropriate, by recrystallization.

Alkyl or aralkyl halides, sulphates or sulphonates, such as, for example, methyl iodide, dimethyl or diethyl sulphate, benzyl chloride or bromide or methyl or ethyl p-toluenesulphonate, can preferably be used to prepare quaternization products of the compounds of the formula (I).

The quaternization products of the compounds of the formula (I) can be obtained in a simple manner by customary methods, such as, for example, by reacting the reaction components in a suitable solvent, such as, for example, acetonitrile or acetone, and they can be isolated in a known manner, for example by precipitation with a suitable precipitating agent, such as, for example, diethyl ether, and filtration with suction, and purified by washing with an inert organic solvent.

The fungicides of group $A_1$ to $A_8$, B, C and D to be used as components in the mixture are already described in the literature; in this context, compare the following data:

($A_1$) Compounds of the formula (IIa): DE-OS (German published specification) No. 1,670,976; German patent specification No. 1,795,249; DE-OS (German published specification) No. 2,128,700 and DE-OS (German published specification) No. 2,628,152.

($A_2$) Compounds of the formula (IIb): DE-OS (German published specification) No. 2,063,857; DE-OS (German published specification) No. 2,105,490; DE-OS (German published specification) No. 2,201,063; DE-OS (German Published Specification) No. 2,324,010; DE-OS (German Published Specification) No. 2,325,156; DE-OS (German Published Specification) No. 2,333,354; DE-OS (German Published Specification) No. 2,431,407; DE-OS (German Published Specification) No. 2,547,953; DE-OS (German Published Specification) No. 2,551,560; DE-OS (German Published Specification) No. 2,600,799; DE-OS (German Published Specification) No. 2,610,022; DE-OS (German Published Specification) No. 2,632,603; DE-OS (German Published Specification) No. 2,635,663; DE-OS (German Published Specification) No. 2,638,470; DE-OS (German Published Specification) No. 2,640,823; DE-OS (German Published Specification) No. 2,654,890; DE-OS (German Published Specification No. 2,720,654; DE-OS (German Published Specification) No. 2,720,949; DE-OS (German Published Specification) No. 2,734,365; DE-OS (German Published Specification) No. 2,734,426; DE-OS (German Published Specification) No. 2,737,489; DE-OS (German Published Specification) No. 2,756,269; DE-OS (German Published Specification) No. 2,800,544; DE-OS (German Published Specification) No. 2,811,919; DE-OS (German Published Specification) No. 2,819,879; DE-OS (German Published Specification) No. 2,832,233; DE-OS (German Published Specification) No. 2,832,234; DE-OS (German Published Specification) No. 2,918,467; DE-OS (German Published Specification) No. 2,926,096; DE-OS (German Published Specification) No. 2,943,631; DE-OS (German Published Specification) No. 2,951,163; DE-OS (German Published Specification) No. 2,951,164; DE-OS (German Published Specification) No. 3,002,430; DE-OS (German Published Specification) No. 3,019,049; DE-OS (German Published Specification) No. 3,048,266; DE-OS (German Published Specification) No. 3,048,267; DE-OS (German Published Specification) No. 3,139,370; DE-OS (German Published Specification) No. 3,209,431; DE-OS (German Published Specification) No. 3,208,194; DE-OS (German Published Specification) No. 3,310,830; European Published Application No. 15,639; European Published Application No. 60,962 and U.S. Pat. No. 4,166,854.

($A_3$) Compounds of the formula (IIc): DE-OS (German Published Specification) No. 2,306,495; DE-OS (German Published Specification) No. 2,335,020; DE-OS (German Published Specification) No. 2,350,122; DE-OS (German Published Specification) No. 2,063,857; DE-OS (German Published Specification) No. 2,735,872 and DE-OS (German Published Specification) No. 2,645,496.

($A_4$) Compounds of the formula (IId): DE-OS (German Published Specification) No. 2,604,047; DE-OS (German Published Specification) No. 2,736,122; DE-OS (German Published Specification) No. 2,920,374; DE-OS (German Published Specification) No. 3,018,866; DE-OS (German Published Specification) No. 3,106,076; DE-OS (German Published Specification) No. 3,202,601; DE-OS (German Published Specification) No. 3,237,400; DE-OS (German Published Specification) No. 3,242,222; DE-OS (German Published Specification) No. 3,242,252; DE-OS (German Published Specification) No. 3,245,504; DE-OS (German Published Specification) No. 3,307,216; European Published Application No. 15,756; European Published Application No. 36,153; European Published Application No. 44,605; European Published Application No. 46,337; European Published Application No. 47,594; European Published Application No. 48,548; European Published Application No. 52,424; European Published Application No. 54,974; European Published Application No. 55,997; European Published Application No. 61,835; European Published Application No. 78,594; European Published Application No. 91,309; European Published Application No. 97,469, European Published Application No. 97,480 and European Published Application No. 101,212.

($A_5$) Compounds of the formula (IIe): DE-OS (German Published Specification) No. 2,645,617; DE-OS (German Published Specification) No. 2,838,847; DE-OS (German Published Specification) No. 2,906,061; DE-OS (German Published Specification) No. 2,929,602; DE-OS (German Published Specification) No. 2,938,422; DE-OS (German Published Specification) No. 3,010,560; DE-OS (German Published Specification) No. 3,025,242 and DE-OS (German Published Specification) No. 3,028,330.

($A_6$) Compounds of the formula (IIf): DE-OS (German Published Specification) No. 2,845,980; DE-OS (German Published Specification) No. 2,928,967; DE-OS (German Published Specification) No. 2,931,755 and European Published Application No. 28,363.

($A_7$) Compounds of the formula (IIg): DE-OS (German Published Specification) No. 2,429,523; DE-OS (German Published Specification) No. 2,856,974 and U.S. Pat. No. 4,208,411.

($A_8$) Compounds of the formula (IIh): European Published Application No. 94,167.

(B) Compounds of the formula (III): DE-OS (German Published Specification) No. 1,770,288 and DE-OS (German Published Specification) No. 2,742,173.

(C) Compounds of the formula (IV): Japanese Patent Application No. 43,334,172

(D) Compounds of the formula (V): DE-OS (German Published Specification) No. 2,830,127.

Particularly preferred partners in the mixtures are: from group ($A_1$)

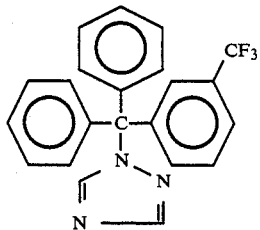

(IIa-1)

from group ($A_2$):

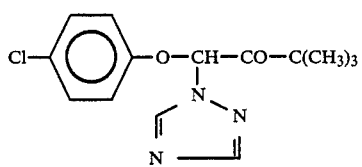 (IIb-1)
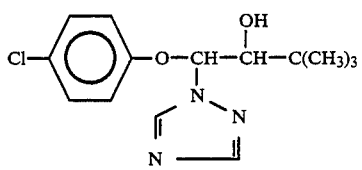 (IIb-2)
from group (A₂):
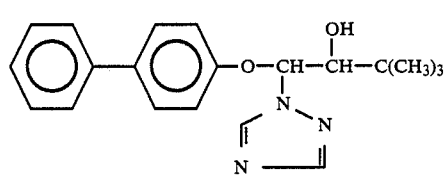 (IIb-3)
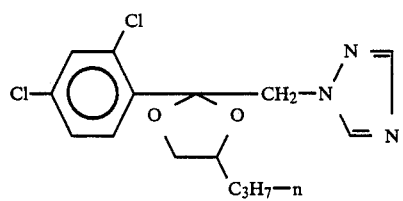 (IIb-4)
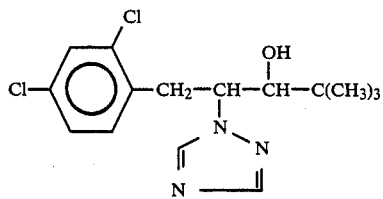 (IIb-5)
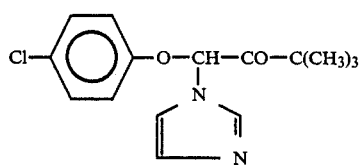 (IIb-6)
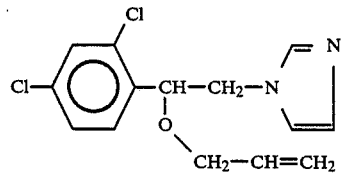 (IIb-7)
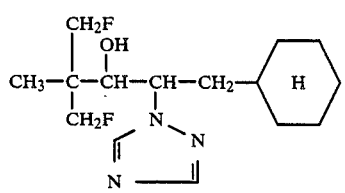 (IIb-8)
-continued
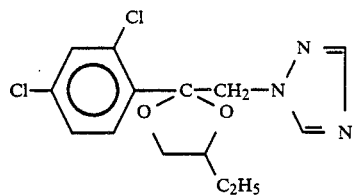 (IIb-9)
from group (A₃):
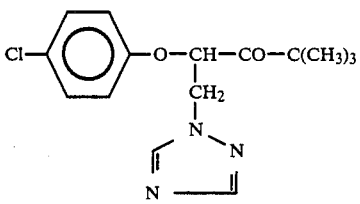 (II c-1)
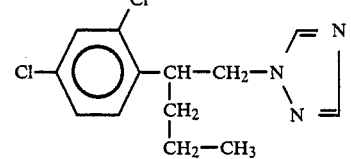 (II c-2)
from group (A₄):
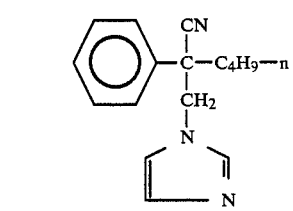 (II d-1)
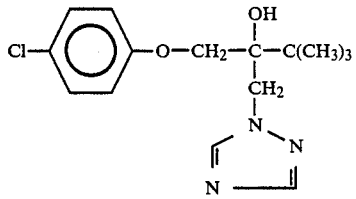 (II d-2)
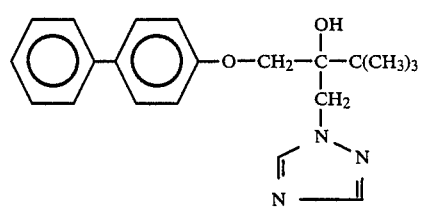 (II d-3)
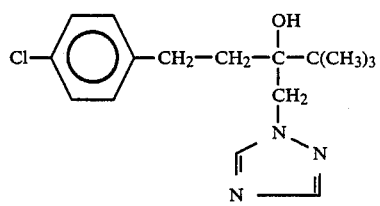 (II d-4)

-continued (II d-5)

from group (A5):

(II e-1)

(II e-2)

(II e-3)

from group (A6):

(II f-1)

from group (A7):

(II g-1)

from group (B)

(III-1)

(III-2)

(III-3)

(III-4)

from group (C):

(IV-1)

and from group (D):

(V-1)

The weight ratios of the groups of active compound in the active compound combinations can vary within relatively wide limits. In general, 0.01 to 50 parts by weight of active compound from active compound classes (A) to (D), preferably 0.02 to 20 parts by weight, and particularly preferably 0.5 to 5 parts by weight of the last group, are present per part by weight of compound of the formula (I).

The active compound combinations according to the invention exhibit a powerful microbicidal action and can be employed in practice for combating undesired micro-organisms. The active compound combinations are suitable for use as plant protection agents, above all as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compound combinations, at the concentrations required for combating plant diseases, permits treatment of above-ground parts of plants, of vegetative propagation stock and seeds, and of the soil.

The active compound combinations according to the invention have a very broad action spectrum and can be used against parasitic fungi which infect the above-ground parts of plants or attack the plants from the soil, as well as seed-borne pathogens. Such active compound combinations are of particular practical importance as seed dressing agents against phytopathogenic fungi which are transmitted with the seed or occur in the soil and attack the crop plants from there. These are seedling diseases, root rot and stalk, stem, leaf, blossom, fruit and seed diseases, which are caused, in particular, by species of Tilletia, Urocystis, Ustilago, Septoria, Typhula, Rhynchosporium, Helminthosphorium and Fusarium. Due to the systemic action of one of the partners in the mixture, the plants are also frequently still protected for a very long time after the dressing from pathogens which can attack various parts of the shoot, for example *Erysiphe graminis* and species of Puccinia. The active compound combinations can also be used as soil treatment agents against phytopathogenic fungi, and have an action against root rot and tracheomycoses, which are caused, for example, by pathogens of the genus Pythium, Verticillium, Phialophora, Rhizoctonia, Fusarium and Thielaviopsis.

However, the active compound combinations according to the invention also exhibit an outstanding action, when applied directly to the above-ground parts of plants, against pathogens on various crop plants, such as powdery mildew fungi (Erysiphe, Uncinula, Sphaerotheca and Podosphaera species and *Leveillula taurica*), rust fungi, Venturia species, Cercospora species, Alternaria species, Botrytis species, Phytophthora species, Peronospora species, *Pyricularia oryzae, Pellicularia sasakii,* Fusarium species, Pyrenophora species, Cochliobolus species, Septoria species and *Pseudocercosporella herpotrichoides.*

When applied in appropriate amounts, the active compound combinations according to the invention also exhibit an insecticidal, acaricidal, insect development-inhibiting, bactericidal and plant growth-regulating action.

The active compound combinations can be converted to the customary formulations, such as solutions, emulsions, wettable powders, suspensions, powders, dusts, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons such as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound combinations according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compound combinations can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The following use examples serve for illustration.

In order to demonstrate synergism between the active compounds used in the following experiments, the results were evaluated by the method described by R. S. Colby (Calculating Synergistic and Antagonistic Responses of Herbicides Combinations; Weeds 15, 20–22, 1967). The expected infestation in % of the untreated control was calculated according to the equation $$E = \frac{X \cdot Y}{100}$$

In this equation, X and Y denote the disease infestation—expressed in % of the untreated control—which the two products allow when used separately. A synergistic effect exists if the fungicidal action of the active compound combination is greater than that of the active compounds applied individually. In this case, the infestation actually observed must be less than the value of the expected infestation (E) calculated from the above-mentioned formula.

EXAMPLE A

*Pyrenophora teres* test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Pyrenophora teres*. The plants then remain in an incubation cabinet at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

TABLE A

| | Pyrenophora teres test (barley)/protective | |
|---|---|---|
| Active compound | Active compound concentration in the spray liquor in % by weight | Disease infestation in % of the untreated control |
| 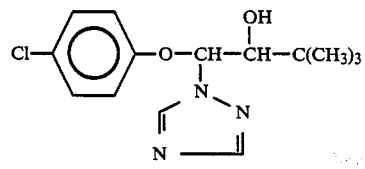 (known) (IIb-2) | 0.005 | 25.0 |
| 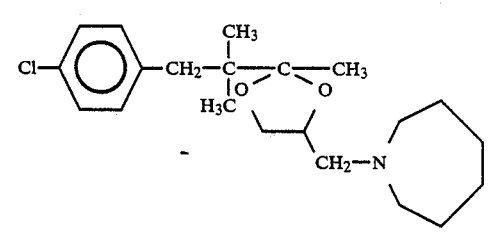 (known) (I-111) | 0.005 | 57.5 |
| 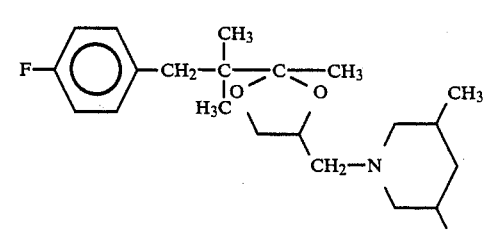 (known) (I-92) | 0.005 | 42.5 |

TABLE A-continued

Pyrenophora teres test (barley)/protective

| | 0.005 | 50.0 |

[Structure: 4-F-C6H4-CH2-C(CH3)(OCH3)-C(CH3)(O-)—CH2-N(azepane), via CH2 on ring O]

(known) (I-87)

| Active compound | Active compound concentration in the spray liquor in % by weight | observed Infestation after using the mixture in % of the untreated control | expected Infestation (E) after using the mixture |
|---|---|---|---|
| Mixture: | | | |
| (IIb-2) + (I-111) = 1:1 | 0.005 + 0.005 | 0.0 | 14.4 |
| (IIb-2) + (I-92) = 1:1 | 0.005 + 0.005 | 0.0 | 10.6 |
| (IIb-2) + (I-87) = 1:1 | 0.005 + 0.005 | 0.0 | 12.5 |

EXAMPLE B

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

TABLE B

Venturia test (apple)/protective

| Active compound | Infestation in % at an active compound concentration of 0.5 ppm |
|---|---|

[Structure: biphenyl-O-CH(triazolyl)-CH(OH)-C(CH3)3]

(known) (IIb-3) — 74

[Structure: 2,4-dichlorophenyl-CH2-C(CH3)(OCH3)-C(CH3)(O-)—CH2-N(3-methylpiperidine)]

(known) (I-140) — 81

[Structure: 4-F-C6H4-CH2-C(CH3)(OCH3)-C(CH3)(O-)—CH2-N(3-methylpiperidine)]

(known) (I-89) — 74

TABLE B-continued

Venturia test (apple)/protective

| Active compound | Infestation in % at an active compound concentration of 0.5 ppm |
|---|---|
| Mixture:<br>(IIb-3) + (I-140) = 1:1<br>(0.5 ppm + 0.5 ppm) | 35 |
| Mixture:<br>(IIb-3) + (I-89) = 1:1<br>(0.5 ppm + 0.5 ppm) | 18 |

PREPARATION EXAMPLES

Example (I-1)

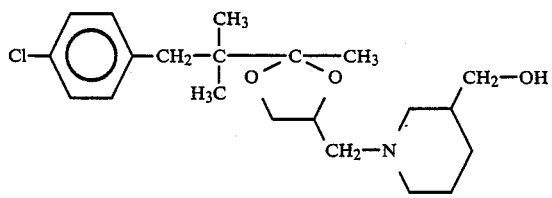

30.3 g (0.1 mole) of 4-chloromethyl-2-[1-(4-chlorophenyl)-2-methyl-prop-2-yl]-2-methyl-1,3-dioxolane, 23 g (0.2 mole) of 3-hydroxymethylpiperidine and 0.1 g of potassium iodide in 100 ml of ethanol are heated at 150° C. under pressure (2 bar) for 15 hours. For working up, the solvent is removed in vacuo, the residue is taken up in 100 ml of methylene chloride, the mixture is washed twice with 100 ml of water each time and dried over sodium sulphate and the solvent is removed again in vacuo.

38 g (100% of theory) of 2-[1-(4-(chlorophenyl)-2-methyl-prop-2-yl]-4-[(3-hydroxymethylpiperidin-1-yl)-2-methyl]-1,3-dioxolane of refractive index $n^{20} = 1.5226$ are obtained.

Example (I-2)

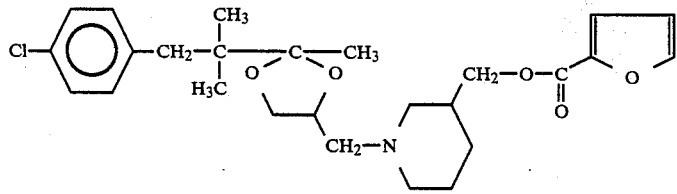

2.4 g (0.0181 mole) of furan-2-carboxylic acid chloride are added to 6.9 g (0.018 mole) of 2-[1-(4-chlorophenyl)-2-methyl-prop-2-yl]-4-[(3-hydroxymethyl-piperidine-1-yl)-methyl]-2-methyl-1,3-dioxolane in 70 ml of methylene chloride at room temperature, with stirring, and the mixture is stirred for a further 2 hours. For working up, 50 ml of saturated sodium bicarbonate solution are added, the organic phase is separated off, the aqueous phase is extracted twice with 50 ml of methylene chloride each time, the combined methylene chloride phases are dried over sodium sulphate and the solvent is removed in vacuo.

6 g (70% of theory) of 2-[1-(4-chlorophenyl)-2-methyl-prop-2-yl]-4-(furyl-2-carbonyloxymethyl)-piperidin-1-yl-methyl]-2-methyl-1,3-dioxolane are obtained as an oil.

$^1$H-NMR (CDCl$_3$): δ=4.17 ppm (d, 2H) corresponds to the

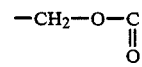

group.

PREPARATION OF THE STARTING SUBSTANCE

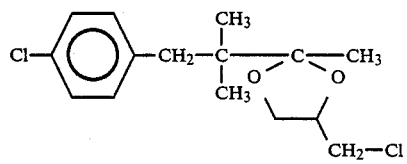

60 g (0.285 mole) of 4-(4-chlorophenyl)-3,3-dimethyl-butan-2-one, 63 g (0.57 mole) of 3-chloropropane-1,2-diol and 5.4 g (0.0285 mole) of p-toluenesulphonic acid are heated in a mixture of 500 ml of toluene and 100 ml of n-butanol under reflux for 15 hours, using a water separator. The solvent is then distilled off under a waterpump vacuum and the residue is subjected to fine distillation under a high vacuum.

After distilling twice, 69 g (80% of theory) of 4-chloromethyl-2-[1-(4-chlorophenyl)-2-methyl-prop-2-yl]-methyl-1,3-dioxolane of boiling point 155° C. under 0.267 mbar are obtained as a cis/trans mixture.

The following compounds of the general formula (Ia) in which Y in formula (I) represents oxygen are obtained in a corresponding manner and in accordance with the general preparation instructions:

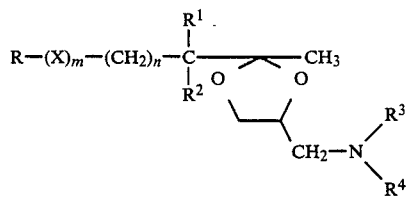

| Example No. | R—(X)$_m$—(CH$_2$)$_n$—C(R$^1$)(R$^2$) | —N(R$^3$)(R$^4$) | Physical constant [Refractive index: n$_D^{20}$ Boiling point: °C./mbar] |
|---|---|---|---|
| (I-3) | 4-F-C$_6$H$_4$-CH$_2$-C(CH$_3$)$_2$- | 2-(hydroxymethyl)piperidin-1-yl | 1.5173 |
| (I-4) | 4-F-C$_6$H$_4$-CH$_2$-C(CH$_3$)$_2$- | 3-(hydroxymethyl)piperidin-1-yl | 1.5123 |
| (I-5) | 4-Cl-C$_6$H$_4$-CH$_2$-C(CH$_3$)$_2$- | 2-(hydroxymethyl)piperidin-1-yl | 1.5269 |
| (I-6) | 2,4-Cl$_2$-C$_6$H$_3$-CH$_2$-C(CH$_3$)$_2$- | 3-(hydroxymethyl)piperidin-1-yl | 1.5308 |
| (I-7) | 3,4-Cl$_2$-C$_6$H$_3$-CH$_2$-C(CH$_3$)$_2$- | 2-(hydroxymethyl)piperidin-1-yl | 1.5361 |
| (I-8) | 3,4-Cl$_2$-C$_6$H$_3$-CH$_2$-C(CH$_3$)$_2$- | 3-(hydroxymethyl)piperidin-1-yl | 1.5362 |
| (I-9) | 4-Cl-C$_6$H$_4$-O-CH$_2$-C(CH$_3$)$_2$- | 2-(hydroxymethyl)piperidin-1-yl | 1.5249 |
| (I-10) | 4-Cl-C$_6$H$_4$-O-CH$_2$-C(CH$_3$)$_2$- | 3-(hydroxymethyl)piperidin-1-yl | 1.5196 |

-continued

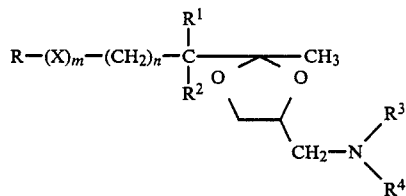

| Example No. | R—(X)$_m$—(CH$_2$)$_n$—C(R$^1$)(R$^2$)— | —N(R$^3$)(R$^4$) | Physical constant [Refractive index: n$_D^{20}$ Boiling point: °C./mbar] |
|---|---|---|---|
| (I-11) | 3,4-Cl$_2$-C$_6$H$_3$-O-CH$_2$-C(CH$_3$)$_2$- | 3-(hydroxymethyl)piperidin-1-yl | 1.5114 |
| (I-12) | 2-CH$_3$-C$_6$H$_4$-O-CH$_2$-C(CH$_3$)$_2$- | 3-(hydroxymethyl)piperidin-1-yl | Oil |
| (I-13) | 2-C$_2$H$_5$-C$_6$H$_4$-O-CH$_2$-C(CH$_3$)$_2$- | 3-(hydroxymethyl)piperidin-1-yl | 1.5041 |
| (I-14) | 3-CH$_3$-6-Cl-C$_6$H$_3$-O-CH$_2$-C(CH$_3$)$_2$- | 3-(hydroxymethyl)piperidin-1-yl | 1.5112 |
| (I-15) | 4-Cl-C$_6$H$_4$-CH$_2$-CH(CH$_3$)- | 3-(hydroxymethyl)piperidin-1-yl | 1.5273 |
| (I-16) | 4-Cl-3-CH$_3$-C$_6$H$_3$-O-C(CH$_3$)$_2$- | 3-(hydroxymethyl)piperidin-1-yl | 250/0.1 |
| (I-17) | 3,4-Cl$_2$-C$_6$H$_3$-O-C(CH$_3$)$_2$- | 3-(hydroxymethyl)piperidin-1-yl | 250/0.1 |
| (I-18) | 3-CH$_3$-C$_6$H$_4$-O-CH$_2$-C(CH$_3$)$_2$- | 3-(hydroxymethyl)piperidin-1-yl | 200/0.1 |

-continued

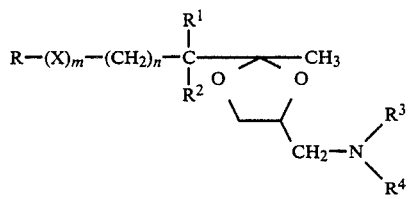

| Example No. | R—(X)$_m$—(CH$_2$)$_n$—C(R$^1$)(R$^2$)— | —N(R$^3$)(R$^4$) | Physical constant [Refractive index: n$_D^{20}$ Boiling point: °C./mbar] |
|---|---|---|---|
| (I-19) | 2,4-dichlorophenyl-O-C(CH$_3$)$_2$— | 3-(hydroxymethyl)piperidin-1-yl | 250/0.1 |
| (I-20) | 3-chlorophenyl-O-CH$_2$-C(CH$_3$)$_2$— | 3-(hydroxymethyl)piperidin-1-yl | 200/0.1 |
| (I-21) | 2-methylphenyl-O-CH$_2$-C(CH$_3$)$_2$— | 3-(hydroxymethyl)piperidin-1-yl | Oil |
| (I-22) | 3-trifluoromethylphenyl-O-C(CH$_3$)$_2$— | 3-(hydroxymethyl)piperidin-1-yl | 1.4810 |
| (I-23) | 4-chloro-3-methylphenyl-OCH$_2$-C(CH$_3$)$_2$— | 3-(hydroxymethyl)piperidin-1-yl | Oil |

Example (I-24)

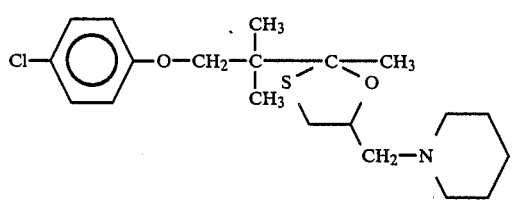

10 g (0.03 mole) of 5-chloromethyl-2-[1-(4-chlorophenoxy)-2-methyl]-prop-2-yl-methyl-1,3-oxathiolane and 10 g (0.12 mole) of piperidine are heated at 120° C. for 12 hours. After cooling, the reaction mixture is diluted with ethyl acetate, washed twice with water, dried over sodium sulphate and concentrated in vacuo. The residue is subjected to bulb tube distillation (boiling point: ~200° C./0.13 mbar) or chromatographed over a silica gel column with an eluant mixture of petroleum ether/ethyl acetate=2:1.

8 g (69.5% of theory) of 2-[1-(4-chlorophenoxy)-2-methyl]-prop-2-yl-methyl-5-piperidin-1-ylmethyl-1,3-oxathiolane of refractive index n$_D^{20}$=1.5440 are obtained.

The compounds listed below of the general formula (Ib) in which Y in formula (I) represents sulphur are obtained in a corresponding manner and in accordance with the general instructions for the preparation:

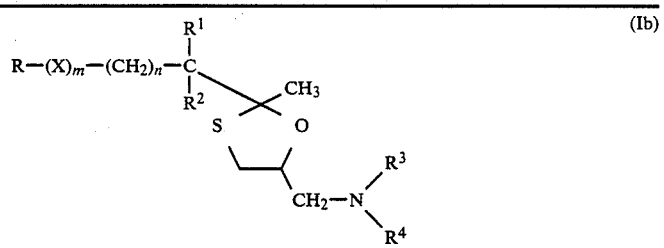

(Ib)

| Example No. | R—(X)$_m$—(CH$_2$)$_n$—C(R$^1$)(R$^2$)— | —N(R$^3$)(R$^4$) | Refractive index [n$_D^{20}$:]; Melting point °C. |
|---|---|---|---|
| (I-25) | 4-Cl-C$_6$H$_4$—O—CH$_2$—C(CH$_3$)$_2$— | 3-methylpiperidin-1-yl | 1.5382 |
| (I-26) | 4-Cl-C$_6$H$_4$—O—CH$_2$—C(CH$_3$)$_2$— | 3,5-dimethylpiperidin-1-yl | 1.5331 |
| (I-27) | 4-Cl-C$_6$H$_4$—O—CH$_2$—C(CH$_3$)$_2$— | 3,3-dimethylpiperidin-1-yl | 1.5357 |
| (I-28) | 4-Cl-C$_6$H$_4$—O—CH$_2$—C(CH$_3$)$_2$— | 2,6-dimethylmorpholin-4-yl | 1.5341 |
| (I-29) | 4-Cl-C$_6$H$_4$—O—CH$_2$—C(CH$_3$)$_2$— | morpholin-4-yl | 1.5039 |
| (I-30) | 4-Cl-C$_6$H$_4$—O—CH$_2$—C(CH$_3$)$_2$— | 4-methylpiperazin-1-yl | 1.5065 |
| (I-31) | 4-Cl-C$_6$H$_4$—O—CH$_2$—C(CH$_3$)$_2$— | 4-phenylpiperazin-1-yl | 1.5147 |
| (I-32) | 4-Cl-C$_6$H$_4$—O—CH$_2$—C(CH$_3$)$_2$— | pyrrolidin-1-yl | 1.5007 |
| (I-33) | 4-Cl-C$_6$H$_4$—O—CH$_2$—C(CH$_3$)$_2$— | 3-(hydroxymethyl)piperidin-1-yl | 1.5077 |

-continued $$R-(X)_m-(CH_2)_n-\underset{R^2}{\underset{|}{\overset{R^1}{\overset{|}{C}}}}-\underset{S}{\overset{CH_3}{\underset{|}{C}}}-\underset{O}{\overset{CH_3}{|}} \quad \text{(Ib)}$$

$$CH_2-N\underset{R^4}{\overset{R^3}{<}}$$

| Example No. | $R-(X)_m-(CH_2)_n-\underset{R^2}{\overset{R^1}{\underset{|}{C}}}$ | $-N\underset{R^4}{\overset{R^3}{<}}$ | Refractive index [$n_D^{20}$]; Melting point °C. |
|---|---|---|---|
| (I-34) | 3-Cl-C₆H₄-O-CH₂-C(CH₃)₂- | 3-methylpiperidinyl | 1.5082 |
| (I-35) | 3-Cl-C₆H₄-O-CH₂-C(CH₃)₂- | 3,5-dimethylpiperidinyl | 1.5049 |
| (I-36) | 3-Cl-C₆H₄-O-CH₂-C(CH₃)₂- | hexamethyleneimino | 1.5058 |
| (I-37) | 2,4-Cl₂-C₆H₃-O-CH₂-C(CH₃)₂- | piperidinyl | 1.5091 |
| (I-38) | 2,4-Cl₂-C₆H₃-O-CH₂-C(CH₃)₂- | 3-methylpiperidinyl | 1.5077 |
| (I-39) | 2,4-Cl₂-C₆H₃-O-CH₂-C(CH₃)₂- | 3,5-dimethylpiperidinyl | 1.5069 |
| (I-40) | 2,4-Cl₂-C₆H₃-O-CH₂-C(CH₃)₂- | 3,3-dimethylpiperidinyl | 1.5087 |
| (I-41) | 2,4-Cl₂-C₆H₃-O-CH₂-C(CH₃)₂- | 4-methylpiperidinyl | 1.5083 |

-continued $$\begin{array}{c} R^1 \\ | \\ R-(X)_m-(CH_2)_n-C \\ | \\ R^2 \end{array} \underset{S}{\overset{CH_3}{\underset{O}{\bigtriangleup}}} \\ CH_2-N \underset{R^4}{\overset{R^3}{\diagdown}}$$ (Ib)

| Example No. | R—(X)$_m$—(CH$_2$)$_n$—C(R$^1$)(R$^2$)— | —N(R$^3$)(R$^4$) | Refractive index [n$_D^{20}$:]; Melting point °C. |
|---|---|---|---|
| (I-42) | 2,4-dichlorophenyl-O-CH$_2$-C(CH$_3$)$_2$- | azepan-1-yl | 1.5110 |
| (I-43) | 4-F-phenyl-CH$_2$-C(CH$_3$)$_2$- | 3-methylpiperidin-1-yl | 1.5245 |
| (I-44) | 2-CH$_3$-phenyl-O-CH$_2$-C(CH$_3$)$_2$- | 3,3-dimethylpiperidin-1-yl | 1.5070 |
| (I-45) | 2-CH$_3$-phenyl-O-CH$_2$-C(CH$_3$)$_2$- | azepan-1-yl | 1.5062 |
| (I-46) | 2-CH$_3$-phenyl-O-CH$_2$-C(CH$_3$)$_2$- | 3,3-dimethyl-5-methyl-azepan-1-yl | 1.5078 |
| (I-47) | 2-C$_2$H$_5$-phenyl-O-CH$_2$-C(CH$_3$)$_2$- | 3-methylpiperidin-1-yl | 1.5122 |
| (I-48) | 2-C$_2$H$_5$-phenyl-O-CH$_2$-C(CH$_3$)$_2$- | 3-(CH$_2$OH)-piperidin-1-yl | 1.5047 |
| (I-49) | 2-C$_2$H$_5$-phenyl-O-CH$_2$-C(CH$_3$)$_2$- | 2,6-dimethylmorpholin-4-yl | 1.5086 (cis form) |

-continued $$R-(X)_m-(CH_2)_n-\underset{R^2}{\overset{R^1}{\underset{|}{C}}}-\underset{S\quad O}{\overset{CH_3}{\underset{|}{C}}}\diagdown$$
$$\overset{|}{\underset{CH_2-N\diagdown_{R^4}^{R^3}}{}}$$ (Ib)

| Example No. | $R-(X)_m-(CH_2)_n-\underset{R^2}{\overset{R^1}{\underset{|}{C}}}-$ | $-N\diagdown_{R^4}^{R^3}$ | Refractive index $[n_D^{20}:]$; Melting point °C. |
|---|---|---|---|
| (I-50) | 4-Cl-C6H4-O-CH2-C(CH3)2- | -N(morpholine with 3,5-di-CH3) | 1.5039 (cis form) |
| (I-51) | 4-Cl-C6H4-O-CH2-C(CH3)2- | -N⊕(CH3)(morpholine with 3,5-di-CH3) O I⊖ | 179–180 |
| (I-52) | 4-Cl-C6H4-O-CH2-C(CH3)2- | -N(CH3)-CH2-CH=C(CH3)2 | Oil |
| (I-53) | 2,4-di-Cl-C6H3-O-C(CH3)2- | -N(morpholine with 3-CH3) | |

Example (I-54)

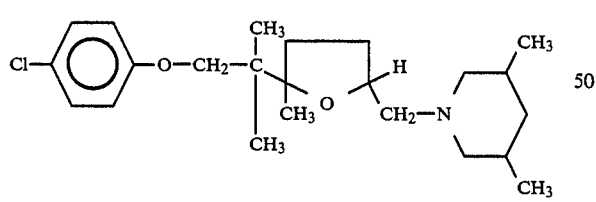

16 g (0.044 mole) of 2-bromomethyl-5-[1-(4-chlorophenoxy)-2-methyl-prop-2-yl]-5-methyl-tetrahydrofuran are stirred together with 11 g (0.097 mole) of cis-3,5-dimethylpiperidine at a bath temperature of 140° C. for about 14 hours. The resulting reaction mixture is taken up in ether, washed several times with water, dried over sodium sulphate and concentrated in vacuo. The oily residue is purified by column chromatography (silica gel 60/ether-petroleum ether 1:1). 7.8 g (45% of theory) of 5-[1-(4-chlorophenoxy)-2-methyl-prop-2-yl]-2-(cis)-(3,5-dimethylpiperidin-1-ylmethyl)-5-methyl-tetrahydrofuran of refractive index $n_D^{20}=1.5049$ are obtained.

PREPARATION OF THE STARTING COMPOUND

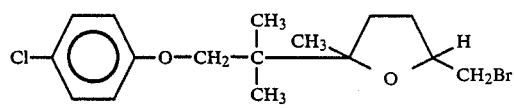

16 g (0.1 mole) of bromine are added dropwise to 28.2 g (0.1 mole) of 7-(4-chlorophenoxy)-5-hydroxy-5,6,6-trimethyl-hept-1-ene in 200 ml of absolute chloroform at room temperature, with stirring, followed by 13 g (0.1 mole) of quinoline, at −10° C. with cooling. The reaction mixture is stirred at room temperature for a further 2 hours and concentrated in vacuo, the residue is taken up in ether, the mixture is filtered and concentrated again in vacuo and the residue is stirred at 95° C. on a water-bath for 1 hour. The resulting mixture is taken up in ether and filtered and the filtrate is washed with 15% strength hydrochloric acid and then with water, dried over sodium sulphate and freed from the solvent in vacuo. 32.7 g (90% of theory) of 2-bromomethyl-5-[1-(4-chlorophenoxy)-2-methylprop-2-yl]-5-methyl-tetrahydrofuran are obtained as an oil, which can be used in the next stage without further purification.

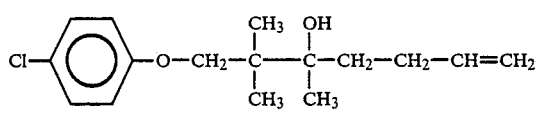

A solution of 48 g (0.2 mole) of 2-[1-(4-chlorophenoxy)-2-methylprop-2-yl]-2-methyl-oxirane in 100 ml of absolute tetrahydrofuran is added dropwise to a Grignard solution of 7.2 g (0.3 mole) of magnesium and 36 g of allyl bromide in 300 ml of absolute ether, while stirring and cooling with ice, and, when the addition has ended, the mixture is heated at the reflux temperature for 4 hours and subsequently stirred at room temperature for 15 hours. For working up, the mixture is hydrolysed with aqueous ammonium chloride solution, the organic phase is separated off and dried over sodium sulphate, the solvent is removed in vacuo and the residue is distilled under a high vacuum.

43 g (51% of theory) of 7-(4-chlorophenoxy)-5-hydroxy-5,6,6-trimethyl-hept-1-ene of boiling point 128° C.–130° C./0.13 mbar are obtained.

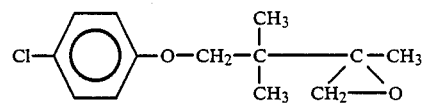

70.2 g (0.33 mole) of sodium methylate are added to a suspension of 72 g (0.33 mole) of trimethylsulphoxonium chloride in 71 g (0.3 mole) of absolute dimethylsulphoxide in the course of 10 minutes, the mixture is then diluted with 100 ml of absolute tetrahydrofuran and subsequently stirred at room temperature for three hours and 68 g (0.3 mole) of 1-(4-chlorophenoxy)-2,2-dimethylbutan-3-one in 50 ml of absolute tetrahydrofuran are then added dropwise. When the addition has ended, the mixture is stirred at room temperature for 2 days, the solid which has precipitated is filtered off, the filtrate is concentrated in vacuo, the residue is dissolved in 300 ml of methylene chloride, the solution is washed several times with a total of 200 ml of water and dried over sodium sulphate and the solvent is removed in vacuo. 62 g (86% of theory) of 2-[1-(4-chlorophenoxy)-2-methyl-prop-2-yl]-1-methyl-oxirane are obtained as an oil, which can be used in the next stage without further purification.

The following compounds of the formula (Ic) in which Y in the formula (I) represents the methylene group were obtained in a corresponding manner and in accordance with the general preparation instructions:

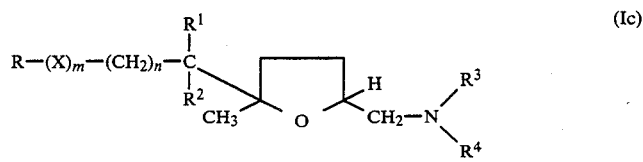

| Example No. | R—(X)$_m$—(CH$_2$)$_n$—$\overset{R^1}{\underset{R^2}{\overset{|}{\underset{|}{C}}}}$— | —N$\overset{R^3}{\underset{R^4}{\diagdown}}$ | Physical constant |
|---|---|---|---|
| (I-58) | 4-Cl-C$_6$H$_4$-O-CH$_2$-C(CH$_3$)$_2$- | 3-methylpiperidino | $n_D^{20}$ = 1.5374 |
| (I-59) | 2,4-Cl$_2$-C$_6$H$_3$-O-CH$_2$-C(CH$_3$)$_2$- | 3,5-dimethylpiperidino | $n_D^{20}$ = 1.5129 (cis form) |

The following compounds of the formula (Id) in which Y in formula (I) represents oxygen are also obtained in a corresponding manner:

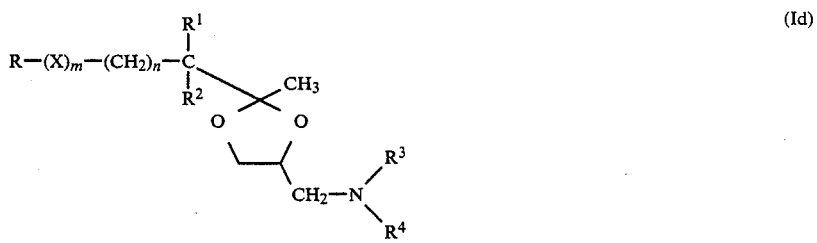

| Example No. | R—(X)$_m$—(CH$_2$)$_n$—$\overset{R^1}{\underset{R^2}{\overset{|}{\underset{|}{C}}}}$— | —N$\overset{R^3}{\underset{R^4}{\diagdown}}$ | Physical constant [Refractive index $n_D^{20}$; melting point °C.] |
|---|---|---|---|
| (I-60) | cyclohexyl-CH$_2$-C(CH$_3$)$_2$- | piperidino | 1.4853 |
| (I-61) | cyclohexyl-CH$_2$-C(CH$_3$)$_2$- | hexamethyleneimino | |
| (I-62) | cyclohexyl-CH$_2$-C(CH$_3$)$_2$- | 3-methylpiperidino | 1.4825 |

-continued $$R-(X)_m-(CH_2)_n-\underset{R^2}{\underset{|}{\overset{R^1}{\underset{|}{C}}}}-\underset{\underset{O}{|}}{\overset{CH_3}{\overset{|}{C}}}-\underset{O}{\overset{CH_3}{|}} \quad\text{(Id)}$$

(with $-CH_2-\underset{CH_2}{\overset{|}{CH}}-N\underset{R^4}{\overset{R^3}{\diagup}}$ on the dioxane ring)

| Example No. | $R-(X)_m-(CH_2)_n-\underset{R^2}{\overset{R^1}{\underset{|}{C}}}-$ | $-N\underset{R^4}{\overset{R^3}{\diagup}}$ | Physical constant [Refractive index $n_D^{20}$; melting point °C.] |
|---|---|---|---|
| (I-63) | cyclohexyl–CH$_2$–C(CH$_3$)$_2$– (H) | 3,5-dimethylpiperidino | 1.4811 |
| (I-64) | 2,4-dichlorophenyl–CH$_2$–CH(CH$_3$)– | piperidino | 1.5195 |
| (I-65) | 2,4-dichlorophenyl–CH$_2$–CH(CH$_3$)– | 2,6-dimethylmorpholino | 1.5123 |
| (I-66) | 2-methoxyphenyl–CH$_2$–CH(CH$_3$)– | hexamethyleneimino (azepan-1-yl) | |
| (I-67) | 2-methoxyphenyl–CH$_2$–CH(CH$_3$)– | 3-methylpiperidino | |
| (I-68) | 4-chlorophenyl–CH$_2$–CH(C$_2$H$_5$)– | piperidino | |
| (I-69) | 4-chlorophenyl–CH$_2$–CH(C$_2$H$_5$)– | hexamethyleneimino | |
| (I-70) | 4-chlorophenyl–CH$_2$–CH(C$_2$H$_5$)– | 3-methylpiperidino | |

-continued

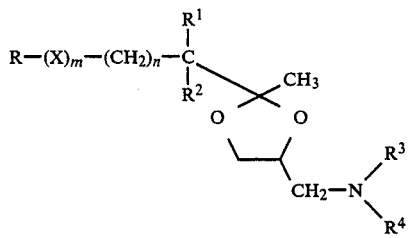

| Example No. | R—(X)$_m$—(CH$_2$)$_n$—C(R$^1$)(R$^2$) | —N(R$^3$)(R$^4$) | Physical constant [Refractive index n$_D^{20}$; melting point °C.] |
|---|---|---|---|
| (I-71) | 4-Cl-C$_6$H$_4$—CH$_2$—CH(C$_2$H$_5$)— | 3,5-dimethylpiperidino | |
| (I-72) | 4-Cl-C$_6$H$_4$—CH$_2$—CH(C$_2$H$_5$)— | 3,3-dimethylpiperidino | |
| (I-73) | 4-Cl-C$_6$H$_4$—CH$_2$—CH(C$_2$H$_5$)— | 2,6-dimethylmorpholino | |
| (I-74) | 2-OCH$_3$-C$_6$H$_4$—CH$_2$—CH(C$_2$H$_5$)— | 3-methylpiperidino | |
| (I-75) | C$_6$H$_5$—CH$_2$—C(CH$_3$)$_2$— | piperidino | 1.5091 |
| (I-76) | C$_6$H$_5$—CH$_2$—CH(CH$_3$)— | piperidino | 1.5149 |
| (I-77) | 2-F-C$_6$H$_4$—CH$_2$—C(CH$_3$)$_2$— | pyrrolidino | 1.5086 |
| (I-78) | 2-F-C$_6$H$_4$—CH$_2$—C(CH$_3$)$_2$— | hexamethyleneimino | 1.5077 |

-continued $$\text{R}-(\text{X})_m-(\text{CH}_2)_n-\underset{\underset{\text{R}^2}{|}}{\overset{\overset{\text{R}^1}{|}}{\text{C}}}\underset{\text{O}\phantom{xx}\text{O}}{\diagdown\phantom{x}\diagup}\overset{\text{CH}_3}{\underset{|}{\text{C}}}\text{CH}_3 \quad \text{(Id)}$$

$$\phantom{xxxxxxxxxxxxxxxx}\text{CH}_2-\text{N}\diagdown\overset{\text{R}^3}{\underset{\text{R}^4}{}}$$

| Example No. | R—(X)$_m$—(CH$_2$)$_n$—C(R$^1$)(R$^2$) | —N(R$^3$)(R$^4$) | Physical constant [Refractive index n$_D^{20}$; melting point °C.] |
|---|---|---|---|
| (I-79) | 2-F-C$_6$H$_4$-CH$_2$-C(CH$_3$)$_2$- | hexamethyleneimino (azepan-1-yl) | 1.5108 |
| (I-80) | 2-F-C$_6$H$_4$-CH$_2$-C(CH$_3$)$_2$- | 2-methylpiperidin-1-yl | 1.5070 |
| (I-81) | 2-F-C$_6$H$_4$-CH$_2$-C(CH$_3$)$_2$- | 3-methylpiperidin-1-yl | 1.5028 |
| (I-82) | 2-F-C$_6$H$_4$-CH$_2$-C(CH$_3$)$_2$- | 4-methylpiperidin-1-yl | 1.5035 |
| (I-83) | 2-F-C$_6$H$_4$-CH$_2$-C(CH$_3$)$_2$- | 3,5-dimethylpiperidin-1-yl | 1.4978 |
| (I-84) | 2-F-C$_6$H$_4$-CH$_2$-C(CH$_3$)$_2$- | 2,6-dimethylmorpholin-4-yl | 1.4996 |
| (I-85) | 4-F-C$_6$H$_4$-CH$_2$-C(CH$_3$)$_2$- | pyrrolidin-1-yl | 1.5069 |
| (I-86) | 4-F-C$_6$H$_4$-CH$_2$-C(CH$_3$)$_2$- | piperidin-1-yl | 1.5061 |

-continued (Id)
$$R-(X)_m-(CH_2)_n-\underset{R^2}{\overset{R^1}{\underset{|}{\overset{|}{C}}}}-\underset{O}{\overset{CH_3}{\underset{|}{\overset{|}{C}}}}-CH_3$$

with CH$_2$-N(R$^3$)(R$^4$) on the dioxolane ring.

| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-87) | 4-F-C$_6$H$_4$-CH$_2$-C(CH$_3$)$_2$- | azepan-1-yl (7-membered ring) | 1.5086 |
| (I-88) | 4-F-C$_6$H$_4$-CH$_2$-C(CH$_3$)$_2$- | 2-methylpiperidin-1-yl | 1.4929 |
| (I-89) | 4-F-C$_6$H$_4$-CH$_2$-C(CH$_3$)$_2$- | 3-methylpiperidin-1-yl | 1.5018 |
| (I-90) | 4-F-C$_6$H$_4$-CH$_2$-C(CH$_3$)$_2$- | 4-methylpiperidin-1-yl | 1.5003 |
| (I-91) | 4-F-C$_6$H$_4$-CH$_2$-C(CH$_3$)$_2$- | 3-(COOC$_2$H$_5$)-piperidin-1-yl | 1.5070 |
| (I-92) | 4-F-C$_6$H$_4$-CH$_2$-C(CH$_3$)$_2$- | 3,5-dimethylpiperidin-1-yl | 1.4952 |
| (I-93) | 4-F-C$_6$H$_4$-CH$_2$-C(CH$_3$)$_2$- | 3,3-dimethylpiperidin-1-yl | 1.4986 |
| (I-94) | 4-F-C$_6$H$_4$-CH$_2$-C(CH$_3$)$_2$- | 3,5-diethylpiperidin-1-yl | 1.5577 |

-continued

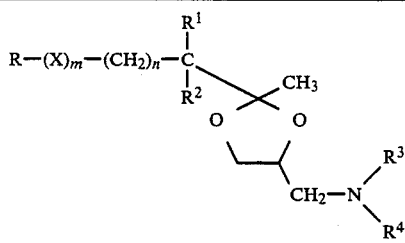
(Id)

| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-95) | 4-F-C$_6$H$_4$-CH$_2$-C(CH$_3$)$_2$- | 2,6-dimethylmorpholin-N-yl | 1.4959 |
| (I-96) | 4-F-C$_6$H$_4$-CH$_2$-C(CH$_3$)$_2$- | 3,3,5-trimethyl-hexahydroazepin-N-yl | 1.5002 |
| (I-97) | 2-Cl-C$_6$H$_4$-CH$_2$-C(CH$_3$)$_2$- | —N(CH$_3$)—CH$_2$—CH=C(CH$_3$)$_2$ | |
| (I-98) | 2-Cl-C$_6$H$_4$-CH$_2$-C(CH$_3$)$_2$- | pyrrolidin-N-yl | 1.5269 |
| (I-99) | 2-Cl-C$_6$H$_4$-CH$_2$-C(CH$_3$)$_2$- | piperidin-N-yl | 1.5239 |
| (I-100) | 2-Cl-C$_6$H$_4$-CH$_2$-C(CH$_3$)$_2$- | hexahydroazepin-N-yl | 1.5272 |
| (I-101) | 2-Cl-C$_6$H$_4$-CH$_2$-C(CH$_3$)$_2$- | 2-methylpiperidin-N-yl | 1.5241 |
| (I-102) | 2-Cl-C$_6$H$_4$-CH$_2$-C(CH$_3$)$_2$- | 3-methylpiperidin-N-yl | 130 |

-continued
(Id)
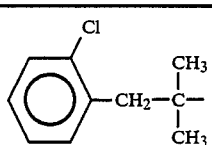
| Example No. | R—(X)$_m$—(CH$_2$)$_n$—C(R$^1$)(R$^2$) | —N(R$^3$)(R$^4$) | Physical constant [Refractive index n$_D^{20}$; melting point °C.] |
|---|---|---|---|
| (I-103) | 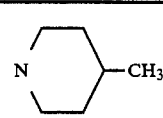 | 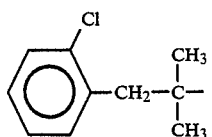 | 1.5193 |
| (I-104) | 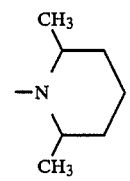 | 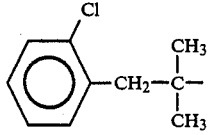 | 1.5375 |
| (I-105) | 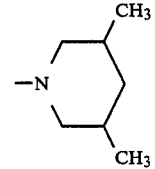 | 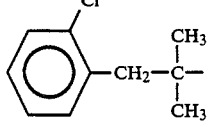 | 1.5162 |
| (I-106) | 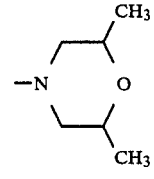 | 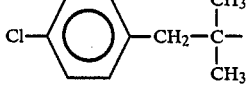 | 1.5208 |
| (I-107) | 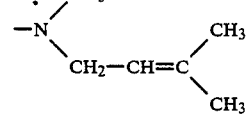 | 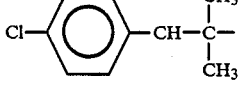 | |
| (I-108) | 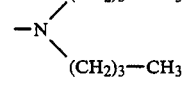 | 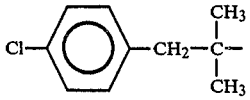 | |
| (I-109) |  | 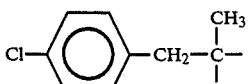 | 1.5261 |
| (I-110) | 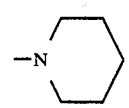 | | 1.5244 |

-continued

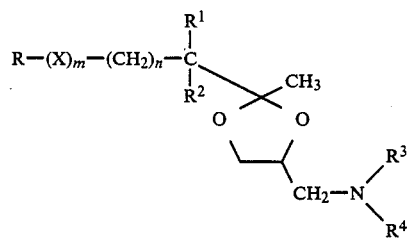
(Id)

| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-111) | 4-Cl-C$_6$H$_4$-CH$_2$-C(CH$_3$)$_2$- | hexamethyleneimino (azepan-1-yl) | 1.5269 |
| (I-112) | 2,4-Cl$_2$-C$_6$H$_3$-CH$_2$-C(CH$_3$)$_2$- | hexamethyleneimino (azepan-1-yl) | 1.5341 |
| (I-113) | 4-Cl-C$_6$H$_4$-CH$_2$-C(CH$_3$)$_2$- | 2-methylpiperidino | 1.5209 |
| (I-114) | 4-Cl-C$_6$H$_4$-CH$_2$-C(CH$_3$)$_2$- | 3-methylpiperidino | 1.5185 |
| (I-115) | 4-Cl-C$_6$H$_4$-CH$_2$-C(CH$_3$)$_2$- | 4-methylpiperidino | 1.5170 |
| (I-116) | 4-Cl-C$_6$H$_4$-CH$_2$-C(CH$_3$)$_2$- | 3,5-dimethylpiperidino | 1.5034 |
| (I-117) | 4-Cl-C$_6$H$_4$-CH$_2$-C(CH$_3$)$_2$- | 3,3-dimethylpiperidino | 1.5154 |
| (I-118) | 4-Cl-C$_6$H$_4$-CH$_2$-C(CH$_3$)$_2$- | 3,3-dimethylpiperidino | 1.5249 |

-continued
$$R-(X)_m-(CH_2)_n-\underset{R^2}{\overset{R^1}{\underset{|}{\overset{|}{C}}}}\overset{CH_3}{\underset{O\diagdown\diagup O}{\diagdown\diagup}}\underset{CH_2-N\overset{R^3}{\diagdown R^4}}{}\quad (Id)$$
| Example No. | $R-(X)_m-(CH_2)_n-\underset{R^2}{\overset{R^1}{\underset{|}{\overset{|}{C}}}}-$ | $-N\overset{R^3}{\diagdown R^4}$ | Physical constant [Refractive index $n_D^{20}$; melting point °C.] |
|---|---|---|---|
| (I-119) | 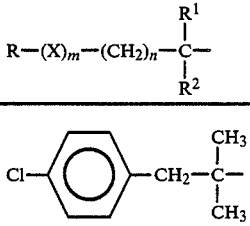 | 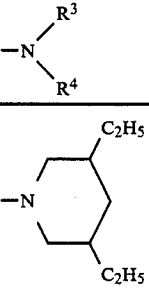 | 1.4982 |
| (I-120) | 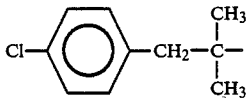 | 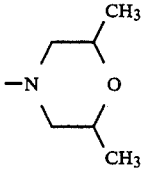 | 1.5154 |
| (I-121) | 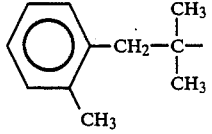 |  | 1.5189 |
| (I-122) | 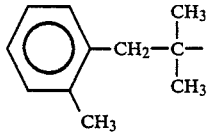 | 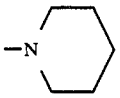 | 1.5177 |
| (I-123) | 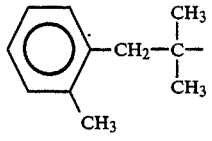 | 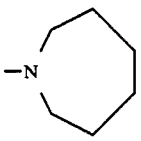 | 1.5189 |
| (I-124) | 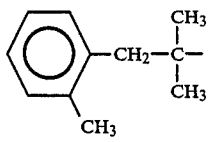 | 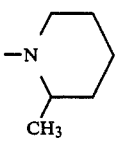 | 1.5177 |
| (I-125) | 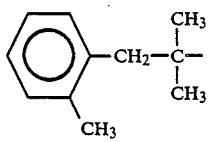 | 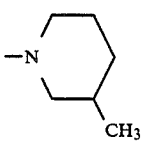 | 1.5178 |

-continued

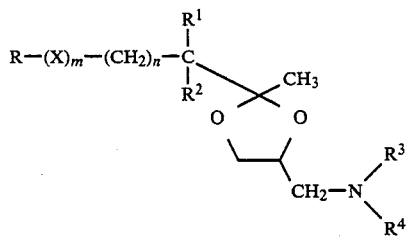
(Id)

| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-126) | 2-CH$_3$-C$_6$H$_4$-CH$_2$-C(CH$_3$)$_2$- | 4-methylpiperidino | 1.5126 |
| (I-127) | 2-CH$_3$-C$_6$H$_4$-CH$_2$-C(CH$_3$)$_2$- | 3,5-dimethylpiperidino | 1.5091 |
| (I-128) | 4-CH$_3$-C$_6$H$_4$-CH$_2$-C(CH$_3$)$_2$- | pyrrolidino | melting point: 170° C. |
| (I-129) | 4-CH$_3$-C$_6$H$_4$-CH$_2$-C(CH$_3$)$_2$- | piperidino | 1.5150 |
| (I-130) | 4-CH$_3$-C$_6$H$_4$-CH$_2$-C(CH$_3$)$_2$- | hexamethyleneimino | 1.5170 |
| (I-131) | 4-CH$_3$-C$_6$H$_4$-CH$_2$-C(CH$_3$)$_2$- | 2-methylpiperidino | 1.5032 |
| (I-132) | 4-CH$_3$-C$_6$H$_4$-CH$_2$-C(CH$_3$)$_2$- | 3-methylpiperidino | 1.5111 |
| (I-133) | 4-CH$_3$-C$_6$H$_4$-CH$_2$-C(CH$_3$)$_2$- | 4-methylpiperidino | 1.5105 |

-continued

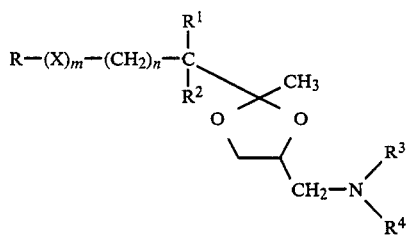

(Id)

| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-134) | 4-CH$_3$-C$_6$H$_4$-CH$_2$-C(CH$_3$)$_2$- | 3,5-dimethylpiperidin-1-yl | 1.5072 |
| (I-135) | 4-CH$_3$-C$_6$H$_4$-CH$_2$-C(CH$_3$)$_2$- | 3,3-dimethylpiperidin-1-yl | 1.5049 |
| (I-136) | 4-CH$_3$-C$_6$H$_4$-CH$_2$-C(CH$_3$)$_2$- | 2,6-dimethylmorpholin-4-yl | 1.5069 |
| (I-137) | 2,4-Cl$_2$-C$_6$H$_3$-CH$_2$-C(CH$_3$)$_2$- | pyrrolidin-1-yl | 1.5346 |
| (I-138) | 2,4-Cl$_2$-C$_6$H$_3$-CH$_2$-C(CH$_3$)$_2$- | piperidin-1-yl | 1.5340 |
| (I-139) | 2,4-Cl$_2$-C$_6$H$_3$-CH$_2$-C(CH$_3$)$_2$- | 2-methylpiperidin-1-yl | boiling point: 220° C./0.2 mbar |
| (I-140) | 2,4-Cl$_2$-C$_6$H$_3$-CH$_2$-C(CH$_3$)$_2$- | 3-methylpiperidin-1-yl | 1.5293 |
| (I-141) | 2,4-Cl$_2$-C$_6$H$_3$-CH$_2$-C(CH$_3$)$_2$- | 4-methylpiperidin-1-yl | 1.5286 |

-continued

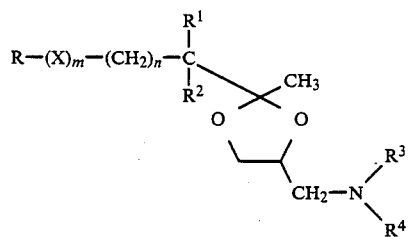
(Id)

| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-142) | 2,4-dichlorophenyl-CH$_2$-C(CH$_3$)$_2$- | 3,5-dimethylpiperidino | 1.5251 |
| (I-143) | 2,4-dichlorophenyl-CH$_2$-C(CH$_3$)$_2$- | 2,6-dimethylmorpholino | 1.5234 |
| (I-144) | 3,4-dichlorophenyl-CH$_2$-C(CH$_3$)$_2$- | piperidino | 73 |
| (I-145) | 3,4-dichlorophenyl-CH$_2$-C(CH$_3$)$_2$- | hexamethyleneimino | 1.5355 |
| (I-146) | 3,4-dichlorophenyl-CH$_2$-C(CH$_3$)$_2$- | 2-methylpiperidino | 1.5297 |
| (I-147) | 3,4-dichlorophenyl-CH$_2$-C(CH$_3$)$_2$- | 3-methylpiperidino | 1.5293 |
| (I-148) | 3,4-dichlorophenyl-CH$_2$-C(CH$_3$)$_2$- | 3,5-dimethylpiperidino | 1.5247 |

-continued

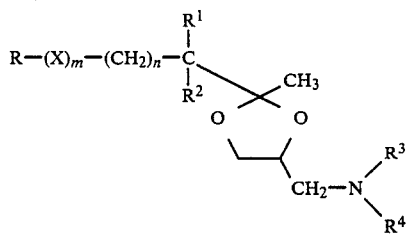
(Id)

| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-149) | 3,4-dichlorobenzyl-C(CH$_3$)$_2$— | 3,5-diethylpiperidin-1-yl | 1.5170 |
| (I-150) | 3,4-dichlorobenzyl-C(CH$_3$)$_2$— | 2,6-dimethylmorpholin-4-yl | 1.5246 |
| (I-151) | 3,4-dichlorobenzyl-C(CH$_3$)$_2$— | 3,3,5-trimethylhexahydroazepin-1-yl | resin |
| (I-152) | phenoxy-C(CH$_3$)$_2$— | piperidin-1-yl | |
| (I-153) | phenoxy-C(CH$_3$)$_2$— | hexahydroazepin-1-yl | |
| (I-154) | phenoxy-C(CH$_3$)$_2$— | 3-methylpiperidin-1-yl | |
| (I-155) | phenoxy-C(CH$_3$)$_2$— | 3,5-dimethylpiperidin-1-yl | |
| (I-156) | phenoxy-C(CH$_3$)$_2$— | 3,3-dimethylpiperidin-1-yl | |

-continued $$R-(X)_m-(CH_2)_n-\underset{R^2}{\overset{R^1}{C}}-\underset{\underset{CH_2-N\overset{R^3}{R^4}}{O\diagdown_{\diagup}O}}{\overset{CH_3}{C}}-CH_3 \quad (Id)$$

| Example No. | $R-(X)_m-(CH_2)_n-\underset{R^2}{\overset{R^1}{C}}-$ | $-N\overset{R^3}{\underset{R^4}{}}$ | Physical constant [Refractive index $n_D^{20}$; melting point °C.] |
|---|---|---|---|
| (I-157) | Ph-O-C(CH₃)₂- | 2,6-dimethylmorpholino | |
| (I-158) | 2-F-C₆H₄-O-C(CH₃)₂- | piperidino | |
| (I-159) | 2-F-C₆H₄-O-C(CH₃)₂- | hexamethyleneimino | |
| (I-160) | 2-F-C₆H₄-O-C(CH₃)₂- | 3-methylpiperidino | 1.5087 |
| (I-161) | 2-F-C₆H₄-O-C(CH₃)₂- | 3,5-dimethylpiperidino | 1.5073 |
| (I-162) | 2-F-C₆H₄-O-C(CH₃)₂- | 3,3-dimethylpiperidino | |
| (I-163) | 2-F-C₆H₄-O-C(CH₃)₂- | 2,6-dimethylmorpholino | |

-continued

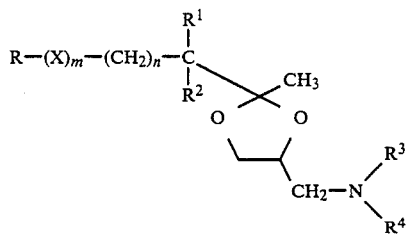
(Id)

| Example No. | R—(X)$_m$—(CH$_2$)$_n$—C(R$^1$)(R$^2$)- | -N(R$^3$)(R$^4$) | Physical constant [Refractive index n$_D^{20}$; melting point °C.] |
|---|---|---|---|
| (I-164) | 4-F-C$_6$H$_4$-O-C(CH$_3$)$_2$- | hexamethyleneimino (azepan-1-yl) | |
| (I-165) | 4-F-C$_6$H$_4$-O-C(CH$_3$)$_2$- | 3-methylpiperidin-1-yl | boiling point: 200° C./0.3 mbar |
| (I-166) | 4-F-C$_6$H$_4$-O-C(CH$_3$)$_2$- | 3,5-dimethylpiperidin-1-yl | boiling point: 190° C./0.2 mbar |
| (I-167) | 4-F-C$_6$H$_4$-O-C(CH$_3$)$_2$- | 3,3-dimethylpiperidin-1-yl | |
| (I-168) | 4-F-C$_6$H$_4$-O-C(CH$_3$)$_2$- | 2,6-dimethylmorpholin-4-yl | |
| (I-169) | 2-Cl-C$_6$H$_4$-O-C(CH$_3$)$_2$- | piperidin-1-yl | |
| (I-170) | 2-Cl-C$_6$H$_4$-O-C(CH$_3$)$_2$- | hexamethyleneimino (azepan-1-yl) | |
| (I-171) | 2-Cl-C$_6$H$_4$-O-C(CH$_3$)$_2$- | 3-methylpiperidin-1-yl | |

-continued $$R-(X)_m-(CH_2)_n-\underset{R^2}{\underset{|}{\overset{R^1}{\underset{|}{C}}}}\underset{O\quad O}{\diagdown\diagup}\underset{CH_3}{\overset{CH_3}{\diagup}} \quad (Id)$$

with CH$_2$—N(R$^3$)(R$^4$) on the dioxolane ring.

| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-172) | 2-Cl-C$_6$H$_4$-O-C(CH$_3$)$_2$- | 3,5-dimethylpiperidino | |
| (I-173) | 2-Cl-C$_6$H$_4$-O-C(CH$_3$)$_2$- | 3,3-dimethylpiperidino | |
| (I-174) | 2-Cl-C$_6$H$_4$-O-C(CH$_3$)$_2$- | 3-methylmorpholino | |
| (I-175) | 4-Cl-C$_6$H$_4$-O-C(CH$_3$)$_2$- | N(CH$_3$)-CH$_2$-CH=C(CH$_3$)$_2$ | |
| (I-176) | 4-Cl-C$_6$H$_4$-O-C(CH$_3$)$_2$- | hexamethyleneimino | 1.5092 |
| (I-177) | 4-Cl-C$_6$H$_4$-O-C(CH$_3$)$_2$- | 3,3-dimethylpiperidino | 1.5062 |
| (I-178) | 4-Cl-C$_6$H$_4$-O-C(CH$_3$)$_2$- | 3,5-dimethylmorpholino | |
| (I-179) | 2-CH$_3$-C$_6$H$_4$-O-C(CH$_3$)$_2$- | piperidino | |

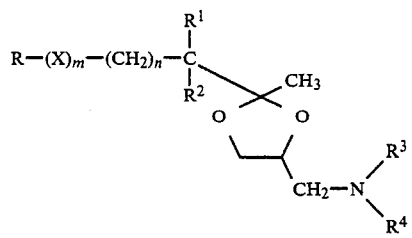
| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-180) | 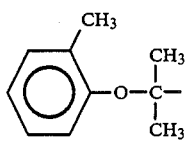 | 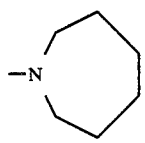 | |
| (I-181) | 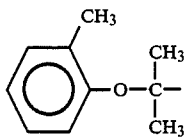 | 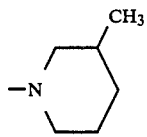 | |
| (I-182) | 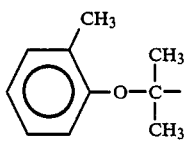 | 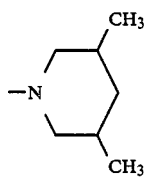 | |
| (I-183) | 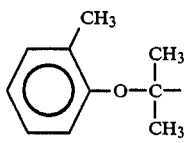 | 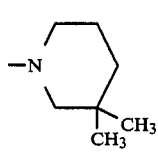 | 1.5039 |
| (I-184) | 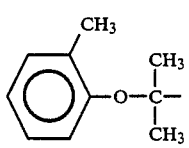 | 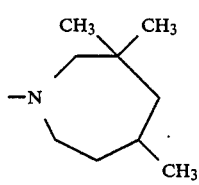 | |
| (I-185) | 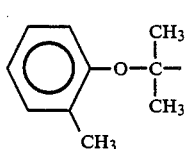 | 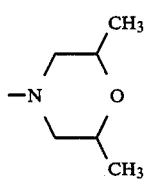 | |
| (I-186) | 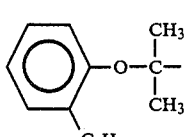 | 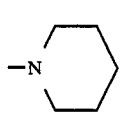 | |

-continued

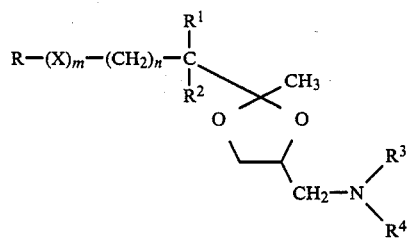
(Id)

| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-187) | 2-ethylphenoxy-C(CH$_3$)$_2$— | 3-methylpiperidin-1-yl | |
| (I-188) | 2-ethylphenoxy-C(CH$_3$)$_2$— | 3,5-dimethylpiperidin-1-yl | |
| (I-189) | 2-ethylphenoxy-C(CH$_3$)$_2$— | 3,3-dimethylpiperidin-1-yl | |
| (I-190) | 2-ethylphenoxy-C(CH$_3$)$_2$— | 2,6-dimethylmorpholin-4-yl | |
| (I-191) | 4-methoxyphenoxy-C(CH$_3$)$_2$— | 3,3-dimethylpiperidin-1-yl | |
| (I-192) | 4-methoxyphenoxy-C(CH$_3$)$_2$— | 2,6-dimethylmorpholin-4-yl | 1.5067 |
| (I-193) | 2,3-dichlorophenoxy-C(CH$_3$)$_2$— | piperidin-1-yl | |

-continued
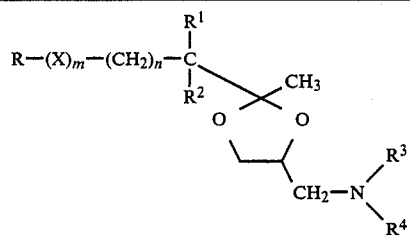
(Id)
| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-194) | 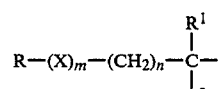 | 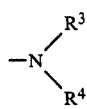 | |
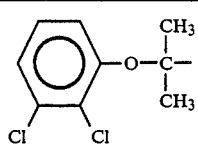
(Id)
| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-195) | 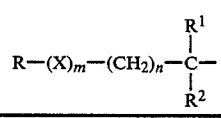 | 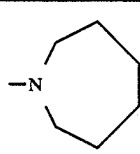 | |
| (I-196) | 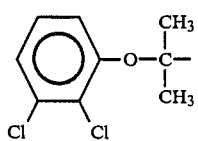 | 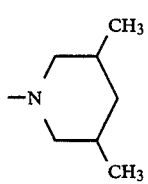 | |
| (I-197) | 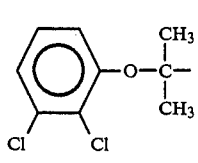 | 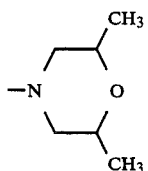 | |
| (I-198) | 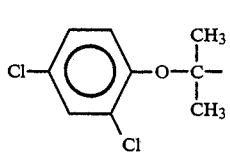 | 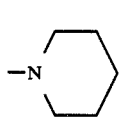 | boiling point: 220° C./0.1 mbar |

-continued

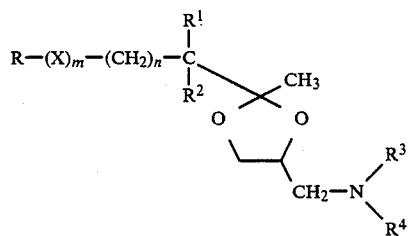
(Id)

| Example No. | R—(X)$_m$—(CH$_2$)$_n$—C(R$^1$)(R$^2$) | —N(R$^3$)(R$^4$) | Physical constant [Refractive index $n_D^{20}$; melting point °C.] |
|---|---|---|---|
| (I-199) | 2,4-Cl$_2$-C$_6$H$_3$-O-C(CH$_3$)$_2$- | azepan-1-yl (7-membered N ring) | boiling point: 250° C./0.1 mbar |
| (I-200) | 2,4-Cl$_2$-C$_6$H$_3$-O-C(CH$_3$)$_2$- | 3-methylpiperidin-1-yl | boiling point: 230° C./0.1 mbar |
| (I-201) | 2,4-Cl$_2$-C$_6$H$_3$-O-C(CH$_3$)$_2$- | 3,3-dimethylpiperidin-1-yl | boiling point: 240° C./0.1 mbar |
| (I-202) | 2,4-Cl$_2$-C$_6$H$_3$-O-C(CH$_3$)$_2$- | 3,5-dimethylpiperidin-1-yl | boiling point: 250° C./0.1 mbar |
| (I-203) | 2,4-Cl$_2$-C$_6$H$_3$-O-C(CH$_3$)$_2$- | 3,5-diethylpiperidin-1-yl | boiling point: 250° C./0.1 mbar |
| (I-204) | 2,4-Cl$_2$-C$_6$H$_3$-O-C(CH$_3$)$_2$- | 2,6-dimethylmorpholin-4-yl | boiling point: 250° C./0.1 mbar |
| (I-205) | 3,4-Cl$_2$-C$_6$H$_3$-O-C(CH$_3$)$_2$- | piperidin-1-yl | boiling point: 240° C./0.1 mbar |

-continued
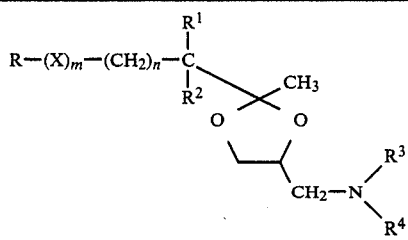 (Id)
| Example No. | R—(X)$_m$—(CH$_2$)$_n$—C(R$^1$)(R$^2$) | —N(R$^3$)(R$^4$) | Physical constant [Refractive index n$_D^{20}$: melting point °C.] |
|---|---|---|---|
| (I-206) | 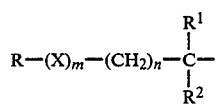 |  | boiling point: 250° C./0.1 mbar |
| (I-207) | 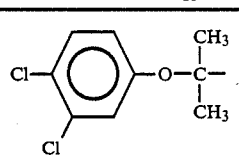 | 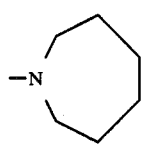 | boiling point: 240° C./0.1 mbar |
| (I-208) | 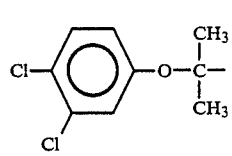 | 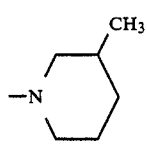 | boiling point: 250° C./0.1 mbar |
| (I-209) | 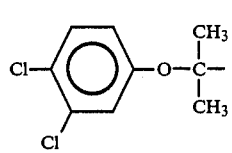 | 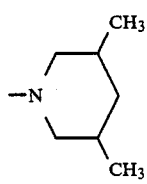 | boiling point: 250° C./0.1 mbar |
| (I-210) | 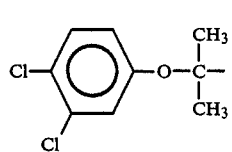 | 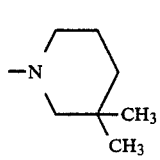 | boiling point: 250° C./0.1 mbar |
| (I-211) | 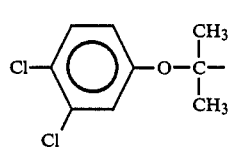 | 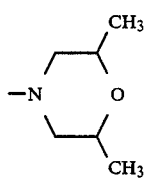 | |
| (I-212) | 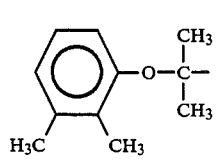 | 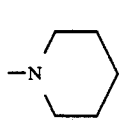 | |
| (I-213) | 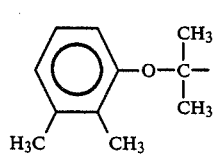 | 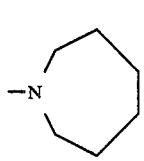 | |
| | 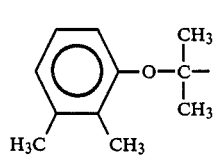 | 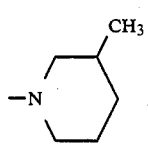 | |

-continued

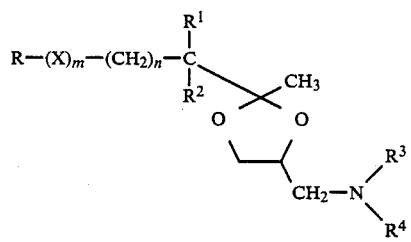
(Id)

| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-214) | 2,3-dimethylphenoxy-C(CH$_3$)$_2$— | 3,5-dimethylpiperidin-1-yl | |
| (I-215) | 2,3-dimethylphenoxy-C(CH$_3$)$_2$— | 3,3-dimethylpiperidin-1-yl | |
| (I-216) | 2,3-dimethylphenoxy-C(CH$_3$)$_2$— | 2,6-dimethylmorpholin-4-yl | |
| (I-217) | 2,3-dimethylphenoxy-C(CH$_3$)$_2$— | hexamethyleneimin-1-yl | 1.5021 |
| (I-218) | 2,3-dimethylphenoxy-C(CH$_3$)$_2$— | 3-methylpiperidin-1-yl | 1.5012 |
| (I-219) | 2,3-dimethylphenoxy-C(CH$_3$)$_2$— | 3,5-dimethylpiperidin-1-yl | 1.5034 |
| (I-220) | 4-chloro-2-methylphenoxy-C(CH$_3$)$_2$— | 3-methylpiperidin-1-yl | boiling point 210° C./0.1 mbar |

-continued

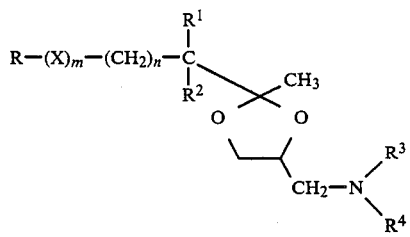

(Id)

| Example No. | R—(X)$_m$—(CH$_2$)$_n$—C(R$^1$)(R$^2$)— | —N(R$^3$)(R$^4$) | Physical constant [Refractive index n$_D^{20}$; melting point °C.] |
|---|---|---|---|
| (I-221) | 4-Cl, 2-CH$_3$-C$_6$H$_3$-O-C(CH$_3$)$_2$- | 3,5-dimethylpiperidin-1-yl | boiling point: 210° C./0.1 mbar |
| (I-222) | 4-Cl, 2-CH$_3$-C$_6$H$_3$-O-C(CH$_3$)$_2$- | piperidin-1-yl | boiling point: 210° C./0.1 mbar |
| (I-223) | 4-Cl, 3-CH$_3$-C$_6$H$_3$-O-C(CH$_3$)$_2$- | hexahydroazepin-1-yl | boiling point 250° C./0.1 mbar |
| (I-224) | 4-Cl, 3-CH$_3$-C$_6$H$_3$-O-C(CH$_3$)$_2$- | 3-methylpiperidin-1-yl | boiling point 230° C./0.1 mbar |
| (I-225) | 4-Cl, 3-CH$_3$-C$_6$H$_3$-O-C(CH$_3$)$_2$- | 3,5-dimethylpiperidin-1-yl | boiling point 240° C./0.1 mbar |
| (I-226) | 4-Cl, 3-CH$_3$-C$_6$H$_3$-O-C(CH$_3$)$_2$- | 3,3-dimethylpiperidin-1-yl | boiling point 230° C./0.1 mbar |
| (I-227) | 4-Cl, 3-CH$_3$-C$_6$H$_3$-O-C(CH$_3$)$_2$- | 3,5-diethylpiperidin-1-yl | boiling point: 230° C./0.1 mbar |

-continued

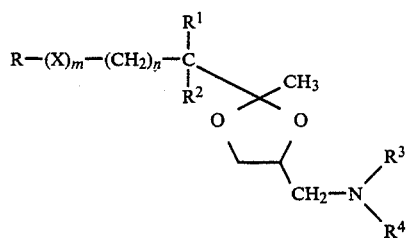

| Example No. | $R-(X)_m-(CH_2)_n-\underset{R^2}{\overset{R^1}{C}}$ | $-N\underset{R^4}{\overset{R^3}{\diagdown}}$ | Physical constant [Refractive index $n_D^{20}$: melting point °C.] |
|---|---|---|---|
| (I-228) | 4-Cl, 3-CH₃-phenyl-O-C(CH₃)₂- | morpholin-2-methyl | boiling point 260° C./0.1 mbar |
| (I-229) | 4-Cl, 2-C₂H₅-phenyl-O-C(CH₃)₂- | hexamethyleneimino | |
| (I-230) | 4-Cl, 2-C₂H₅-phenyl-O-C(CH₃)₂- | 3-methylpiperidino | |
| (I-231) | 4-Cl, 2-C₂H₅-phenyl-O-C(CH₃)₂- | 3,5-dimethylpiperidino | |
| (I-232) | 4-CH₃S, 3-CH₃-phenyl-O-C(CH₃)₂- | 3-methylpiperidino | 1.5027 |
| (I-233) | 4-CH₃S, 3-CH₃-phenyl-O-C(CH₃)₂- | 3,5-dimethylpiperidino | 1.5041 |
| (I-234) | 4-Cl, 3,5-(CH₃)₂-phenyl-O-C(CH₃)₂- | piperidino | |

-continued
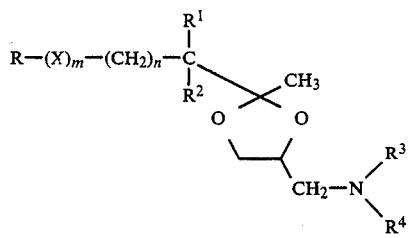
| Example No. | R—(X)$_m$—(CH$_2$)$_n$—$\overset{R^1}{\underset{R^2}{C}}$— | —N$\overset{R^3}{\underset{R^4}{}}$ | Physical constant [Refractive index n$_D^{20}$: melting point °C.] |
|---|---|---|---|
| (I-235) | 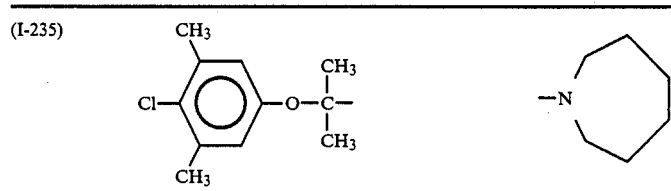 | 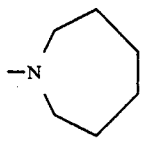 | |
| (I-236) | 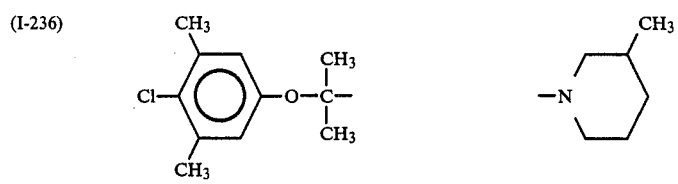 | 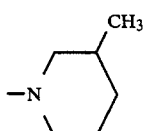 | |
| (I-237) | 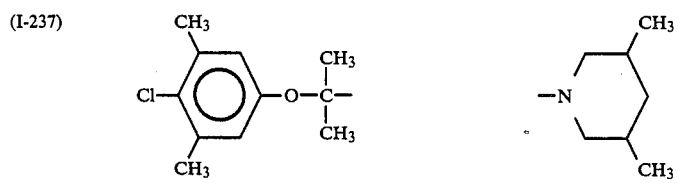 | 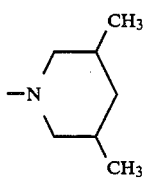 | |
| (I-238) | 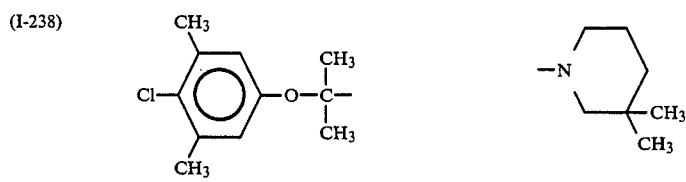 | 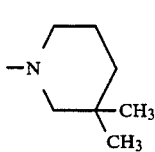 | |
| (I-239) | 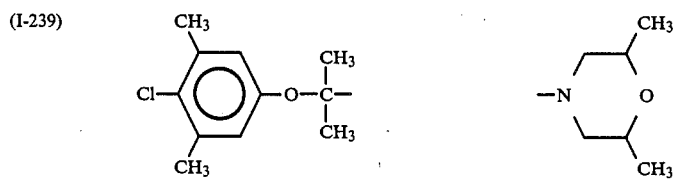 | 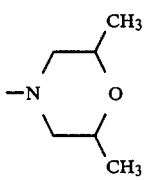 | |
| (I-240) | 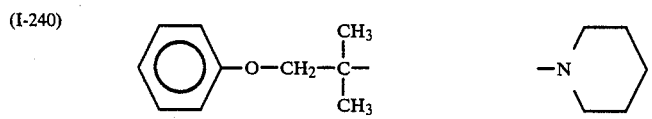 | 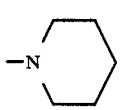 | |
| (I-241) | 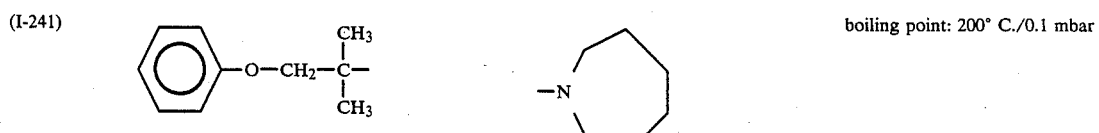 | 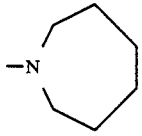 | boiling point: 200° C./0.1 mbar |

-continued

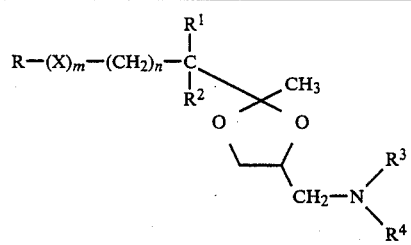
(Id)

| Example No. | R—(X)$_m$—(CH$_2$)$_n$—C(R$^1$)(R$^2$)— | —N(R$^3$)(R$^4$) | Physical constant [Refractive index n$_D^{20}$: melting point °C.] |
|---|---|---|---|
| (I-242) | PhO—CH$_2$—C(CH$_3$)$_2$— | 2-methylpiperidin-1-yl | 1,4998 |
| (I-243) | PhO—CH$_2$—C(CH$_3$)$_2$— | 3-methylpiperidin-1-yl | 1,4973 boiling point: 200° C./0.1 mbar |
| (I-244) | PhO—CH$_2$—C(CH$_3$)$_2$— | 4-methylpiperidin-1-yl | 1,4939 |
| (I-245) | PhO—CH$_2$—C(CH$_3$)$_2$— | 3,5-dimethylpiperidin-1-yl | 1.4972 |
| (I-246) | PhO—CH$_2$—C(CH$_3$)$_2$— | 3-methylmorpholin-4-yl | 1.4925 |
| (I-247) | PhO—CH$_2$—C(CH$_3$)$_2$— | 4-methylpiperazin-1-yl | 1.5031 |
| (I-248) | 4-F-C$_6$H$_4$—O—CH$_2$—C(CH$_3$)$_2$— | —N((CH$_2$)$_3$CH$_3$)$_2$ | 1.4702 |
| (I-249) | 4-F-C$_6$H$_4$—O—CH$_2$—C(CH$_3$)$_2$— | pyrrolidin-1-yl | 1.4912 |
| (I-250) | 4-F-C$_6$H$_4$—O—CH$_2$—C(CH$_3$)$_2$— | piperidin-1-yl | 1.4907 |

-continued

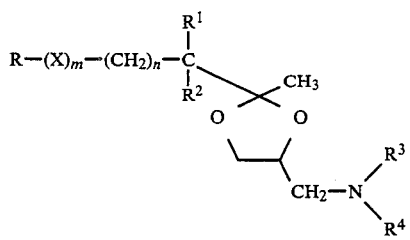

(Id)

| Example No. | R—(X)$_m$—(CH$_2$)$_n$—$\underset{R^2}{\overset{R^1}{\underset{|}{\overset{|}{C}}}}$— | —N$\overset{R^3}{\underset{R^4}{\diagdown}}$ | Physical constant [Refractive index n$_D^{20}$: melting point °C.] |
|---|---|---|---|
| (I-251) | F—⟨C$_6$H$_4$⟩—O—CH$_2$—C(CH$_3$)$_2$— | —N(azepane) | 1.4930 |
| (I-252) | F—⟨C$_6$H$_4$⟩—O—CH$_2$—C(CH$_3$)$_2$— | —N(morpholine) | 1.4921 |
| (I-253) | F—⟨C$_6$H$_4$⟩—O—CH$_2$—C(CH$_3$)$_2$— | —N(2-methylpiperidine) | 1.4897 |
| (I-254) | F—⟨C$_6$H$_4$⟩—O—CH$_2$—C(CH$_3$)$_2$— | —N(3-methylpiperidine) | 1.4873 |
| (I-255) | F—⟨C$_6$H$_4$⟩—O—CH$_2$—C(CH$_3$)$_2$— | —N(4-methylpiperidine) | 1.4868 |
| (I-256) | F—⟨C$_6$H$_4$⟩—O—CH$_2$—C(CH$_3$)$_2$— | —N(4-phenylpiperidine) | 1.5118 |
| (I-257) | F—⟨C$_6$H$_4$⟩—O—CH$_2$—C(CH$_3$)$_2$— | —N(3,5-dimethylpiperidine) | 1.4841 |
| (I-258) | F—⟨C$_6$H$_4$⟩—O—CH$_2$—C(CH$_3$)$_2$— | —N(2,6-dimethylpiperidine) | 1.4893 |

-continued

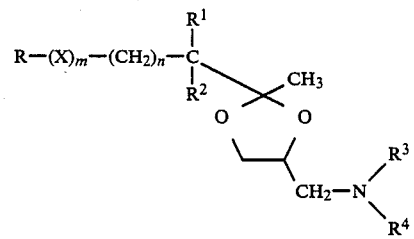
(Id)

| Example No. | R—(X)$_m$—(CH$_2$)$_n$—C(R$^1$)(R$^2$) | —N(R$^3$)(R$^4$) | Physical constant [Refractive index n$_D^{20}$: melting point °C.] |
|---|---|---|---|
| (I-259) | 4-F-C$_6$H$_4$—O—CH$_2$—C(CH$_3$)$_2$— | 2,4-dimethylpiperidin-1-yl | 1.4864 |
| (I-260) | 4-F-C$_6$H$_4$—O—CH$_2$—C(CH$_3$)$_2$— | 3,3-dimethylpiperidin-1-yl | 1.4825 |
| (I-261) | 4-F-C$_6$H$_4$—O—CH$_2$—C(CH$_3$)$_2$— | 2,6-dimethylmorpholin-4-yl | 1.4839 |
| (I-262) | 2-Cl-C$_6$H$_4$—O—CH$_2$—C(CH$_3$)$_2$— | pyrrolidin-1-yl | 1.5064 |
| (I-263) | 2-Cl-C$_6$H$_4$—O—CH$_2$—C(CH$_3$)$_2$— | piperidin-1-yl | 1.5082 |
| (I-264) | 2-Cl-C$_6$H$_4$—O—CH$_2$—C(CH$_3$)$_2$— | hexamethyleneimin-1-yl | 1.5090 |
| (I-265) | 2-Cl-C$_6$H$_4$—O—CH$_2$—C(CH$_3$)$_2$— | morpholin-4-yl | 1.5089 |
| (I-266) | 2-Cl-C$_6$H$_4$—O—CH$_2$—C(CH$_3$)$_2$— | 2-methylpiperidin-1-yl | 1.5047 |

-continued

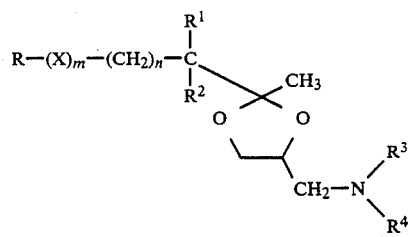
(Id)

| Example No. | R—(X)$_m$—(CH$_2$)$_n$—C(R$^1$)(R$^2$)— | —N(R$^3$)(R$^4$) | Physical constant [Refractive index n$_D^{20}$: melting point °C.] |
|---|---|---|---|
| (I-267) | 2-Cl-C$_6$H$_4$-O-CH$_2$-C(CH$_3$)$_2$- | 3-methylpiperidin-1-yl | 1.5051 |
| (I-268) | 2-Cl-C$_6$H$_4$-O-CH$_2$-C(CH$_3$)$_2$- | 4-methylpiperidin-1-yl | 1.5044 |
| (I-269) | 2-Cl-C$_6$H$_4$-O-CH$_2$-C(CH$_3$)$_2$- | 4-(ethoxycarbonyl)piperidin-1-yl | 1.5044 |
| (I-270) | 2-Cl-C$_6$H$_4$-O-CH$_2$-C(CH$_3$)$_2$- | 4-methylpiperazin-1-yl | 1.5021 |
| (I-271) | 2-Cl-C$_6$H$_4$-O-CH$_2$-C(CH$_3$)$_2$- | 2,6-dimethylpiperidin-1-yl | 1.5076 |
| (I-272) | 2-Cl-C$_6$H$_4$-O-CH$_2$-C(CH$_3$)$_2$- | 3,3-dimethylpiperidin-1-yl | 1.5045 |
| (I-273) | 2-Cl-C$_6$H$_4$-O-CH$_2$-C(CH$_3$)$_2$- | 3,5-dimethylpiperidin-1-yl | 1.5047 |
| (I-274) | 2-Cl-C$_6$H$_4$-O-CH$_2$-C(CH$_3$)$_2$- | 2,4-dimethylpiperidin-1-yl | 1.5040 |

-continued

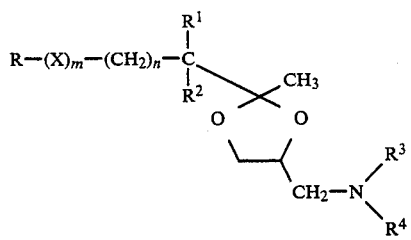
(Id)

| Example No. | R—(X)$_m$—(CH$_2$)$_n$—C(R$^1$)(R$^2$) | —N(R$^3$)(R$^4$) | Physical constant [Refractive index n$_D^{20}$: melting point °C.] |
|---|---|---|---|
| (I-275) | 2-Cl-C$_6$H$_4$—O—CH$_2$—C(CH$_3$)$_2$— | 2,6-dimethylmorpholin-4-yl | 1.5062 |
| (I-276) | 4-Cl-C$_6$H$_4$—O—CH$_2$—C(CH$_3$)$_2$— | piperidin-1-yl | 1.5073 |
| (I-277) | 3-Cl-C$_6$H$_4$—O—CH$_2$—C(CH$_3$)$_2$— | hexahydroazepin-1-yl | 1.4995 |
| (I-278) | 4-Cl-C$_6$H$_4$—O—CH$_2$—C(CH$_3$)$_2$— | 3-methylpiperidin-1-yl | 1.5073 |
| (I-279) | 4-Cl-C$_6$H$_4$—O—CH$_2$—C(CH$_3$)$_2$— | 3,3-dimethylpiperidin-1-yl | 1.4995 |
| (I-280) | 4-Cl-C$_6$H$_4$—O—CH$_2$—C(CH$_3$)$_2$— | 2,6-dimethylmorpholin-4-yl | 1.4970 boiling point: 200° C./0.1 mbar |
| (I-281) | 4-Cl-C$_6$H$_4$—O—CH$_2$—C(CH$_3$)$_2$— | —N(C$_4$H$_9$-n)$_2$ | 1.5377 |
| (I-282) | 4-Cl-C$_6$H$_4$—O—CH$_2$—C(CH$_3$)$_2$— | —N(CH$_3$)(CH$_2$—CH=C(CH$_3$)$_2$) | 1.5097 |

-continued

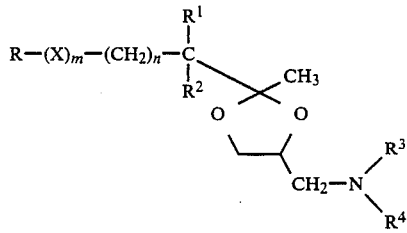
(Id)

| Example No. | R—(X)$_m$—(CH$_2$)$_n$—C(R$^1$)(R$^2$)— | —N(R$^3$)(R$^4$) | Physical constant [Refractive index n$_D^{20}$: melting point °C.] |
|---|---|---|---|
| (I-283) | Cl—C$_6$H$_4$—O—CH$_2$—C(CH$_3$)$_2$— | piperidin-1-yl (5-membered, pyrrolidine) | 1.5200 |
| (I-284) | Cl—C$_6$H$_4$—O—CH$_2$—C(CH$_3$)$_2$— | piperidin-1-yl | 1.5121 |
| (I-285) | Cl—C$_6$H$_4$—O—CH$_2$—C(CH$_3$)$_2$— | piperidin-1-yl (xHCl) | melting point: 153–155° C. |
| (I-286) | Cl—C$_6$H$_4$—O—CH$_2$—C(CH$_3$)$_2$— | hexamethyleneimin-1-yl | 1.5079 |
| (I-287) | Cl—C$_6$H$_4$—O—CH$_2$—C(CH$_3$)$_2$— | morpholin-4-yl | 1.5191 |
| (I-288) | Cl—C$_6$H$_4$—O—CH$_2$—C(CH$_3$)$_2$— | 2-methylpiperidin-1-yl | 1.5102 |
| (I-289) | Cl—C$_6$H$_4$—O—CH$_2$—C(CH$_3$)$_2$— | 3-methylpiperidin-1-yl | 1.5045 |
| (I-290) | Cl—C$_6$H$_4$—O—CH$_2$—C(CH$_3$)$_2$— | 4-methylpiperidin-1-yl | 1.5040 |
| (I-291) | Cl—C$_6$H$_4$—O—CH$_2$—C(CH$_3$)$_2$— | 4-phenylpiperidin-1-yl | 1.5431 |
| (I-292) | Cl—C$_6$H$_4$—O—CH$_2$—C(CH$_3$)$_2$— | 4-methylpiperazin-1-yl | 1.5082 |

-continued

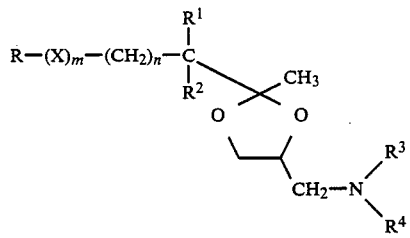
(Id)

| Example No. | R—(X)$_m$—(CH$_2$)$_n$—C(R$^1$)(R$^2$)— | NR$^3$R$^4$ | Physical constant [Refractive index n$_D^{20}$: melting point °C.] |
|---|---|---|---|
| (I-293) | Cl-C$_6$H$_4$-O-CH$_2$-C(CH$_3$)$_2$- | -N(piperazine)N-COOC$_2$H$_5$ | 1.4993 |
| (I-294) | Cl-C$_6$H$_4$-O-CH$_2$-C(CH$_3$)$_2$- | -N(2-CH$_3$, 4-CH$_3$-piperidine) | 1.5031 |
| (I-295) | Cl-C$_6$H$_4$-O-CH$_2$-C(CH$_3$)$_2$- | -N(3-CH$_3$, 5-CH$_3$-piperidine) | 1.5000 |
| (I-296) | Cl-C$_6$H$_4$-O-CH$_2$-C(CH$_3$)$_2$- | -N(3,3-di-CH$_3$-piperidine) | 1.5105 |
| (I-297) | Cl-C$_6$H$_4$-O-CH$_2$-C(CH$_3$)$_2$- | -N(3-C$_2$H$_5$, 5-C$_2$H$_5$-piperidine) | |
| (I-298) | Cl-C$_6$H$_4$-O-CH$_2$-C(CH$_3$)$_2$- | -N(2-CH$_3$, 6-CH$_3$-morpholine) | 1.5361 |
| (I-299) | 2-CH$_3$-C$_6$H$_4$-O-CH$_2$-C(CH$_3$)$_2$- | -N(piperidine) | 1.4952 |
| (I-300) | 2-CH$_3$-C$_6$H$_4$-O-CH$_2$-C(CH$_3$)$_2$- | -N(morpholine) | 1.5002 |

-continued

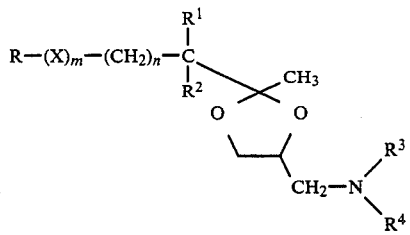
(Id)

| Example No. | R—(X)$_m$—(CH$_2$)$_n$—C(R$^1$)(R$^2$) | —N(R$^3$)(R$^4$) | Physical constant [Refractive index n$_D^{20}$; melting point °C.] |
|---|---|---|---|
| (I-301) | 2-CH$_3$-C$_6$H$_4$-O-CH$_2$-C(CH$_3$)$_2$- | hexamethyleneimino (azepan-1-yl) | 1.4995 |
| (I-302) | 2-CH$_3$-C$_6$H$_4$-O-CH$_2$-C(CH$_3$)$_2$- | 3,5-dimethylpiperidin-1-yl | 1.4909 |
| (I-303) | 2-CH$_3$-C$_6$H$_4$-O-CH$_2$-C(CH$_3$)$_2$- | 4,4-dimethylpiperidin-1-yl | 1.4908 |
| (I-304) | 2-CH$_3$-C$_6$H$_4$-O-CH$_2$-C(CH$_3$)$_2$- | 2,6-dimethylmorpholin-4-yl | 1.4874 |
| (I-305) | 3-CH$_3$-C$_6$H$_4$-O-CH$_2$-C(CH$_3$)$_2$- | 4-methylpiperazin-1-yl | 1.5023 |
| (I-306) | 3-CH$_3$-C$_6$H$_4$-O-CH$_2$-C(CH$_3$)$_2$- | 3,5-dimethylpiperidin-1-yl | boiling point: 200° C./0.1 mbar |
| (I-307) | 3-CH$_3$-C$_6$H$_4$-O-CH$_2$-C(CH$_3$)$_2$- | 2,6-dimethylmorpholin-4-yl | boiling point: 200° C./0.1 mbar |
| (I-308) | 4-CH$_3$-C$_6$H$_4$-O-CH$_2$-C(CH$_3$)$_2$- | di-n-butylamino | 1.5132 |

-continued

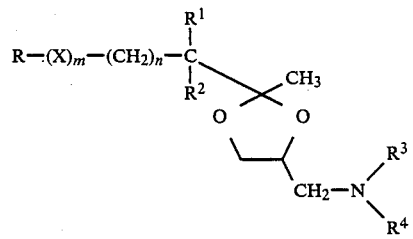

(Id)

| Example No. | R—(X)$_m$—(CH$_2$)$_n$—C(R$^1$)(R$^2$)— | —N(R$^3$)(R$^4$) | Physical constant [Refractive index n$_D^{20}$: melting point °C.] |
|---|---|---|---|
| (I-309) | CH$_3$—C$_6$H$_4$—O—CH$_2$—C(CH$_3$)$_2$— | piperidino | Oil |
| (I-310) | CH$_3$—C$_6$H$_4$—O—CH$_2$—C(CH$_3$)$_2$— | hexamethyleneimino | 1.5118 |
| (I-311) | CH$_3$—C$_6$H$_4$—O—CH$_2$—C(CH$_3$)$_2$— | morpholino | Oil |
| (I-312) | CH$_3$—C$_6$H$_4$—O—CH$_2$—C(CH$_3$)$_2$— | 3-methylpiperidino | Oil |
| (I-313) | CH$_3$—C$_6$H$_4$—O—CH$_2$—C(CH$_3$)$_2$— | 3,5-dimethylpiperidino | Oil |
| (I-314) | 2-C$_2$H$_5$—C$_6$H$_4$—O—CH$_2$—C(CH$_3$)$_2$— | pyrrolidino | 1.5110 |
| (I-315) | 2-C$_2$H$_5$—C$_6$H$_4$—O—CH$_2$—C(CH$_3$)$_2$— | piperidino | 1.5087 |
| (I-316) | 2-C$_2$H$_5$—C$_6$H$_4$—O—CH$_2$—C(CH$_3$)$_2$— | hexamethyleneimino | 1.5094 |

-continued

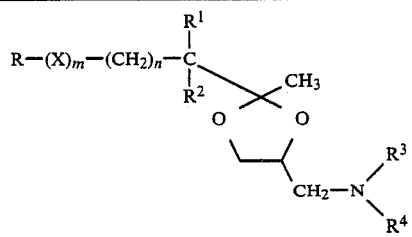
(Id)

| Example No. | R—(X)$_m$—(CH$_2$)$_n$—C(R$^1$)(R$^2$) | —N(R$^3$)(R$^4$) | Physical constant [Refractive index n$_D^{20}$: melting point °C.] |
|---|---|---|---|
| (I-317) | 2-ethylphenyl-O-CH$_2$-C(CH$_3$)$_2$- | morpholino | 1.5076 |
| (I-318) | 2-ethylphenyl-O-CH$_2$-C(CH$_3$)$_2$- | 3-methylpiperidino | 1.5042 |
| (I-319) | 2-ethylphenyl-O-CH$_2$-C(CH$_3$)$_2$- | 4-methylpiperidino | 1.5067 |
| (I-320) | 2-ethylphenyl-O-CH$_2$-C(CH$_3$)$_2$- | 4-methylpiperazino | 1.5046 |
| (I-321) | 2-ethylphenyl-O-CH$_2$-C(CH$_3$)$_2$- | 3,5-dimethylpiperidino | 1.5047 |
| (I-322) | 2-ethylphenyl-O-CH$_2$-C(CH$_3$)$_2$- | 3,3-dimethylpiperidino | 1.5071 |
| (I-323) | 2-ethylphenyl-O-CH$_2$-C(CH$_3$)$_2$- | 2,6-dimethylmorpholino | 1.5031 |
| (I-324) | 2-ethylphenyl-O-CH$_2$-C(CH$_3$)$_2$- | 3,3,5-trimethylhexahydroazepino | 1.5119 |

-continued

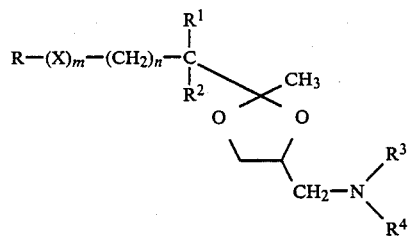
(Id)

| Example No. | R—(X)$_m$—(CH$_2$)$_n$—C(R$^1$)(R$^2$)— | —N(R$^3$)(R$^4$) | Physical constant [Refractive index n$_D^{20}$: melting point °C.] |
|---|---|---|---|
| (I-325) | t-C$_4$H$_9$—C$_6$H$_4$—O—CH$_2$—C(CH$_3$)$_2$— | pyrrolidino | 1.4948 |
| (I-326) | t-C$_4$H$_9$—C$_6$H$_4$—O—CH$_2$—C(CH$_3$)$_2$— | piperidino | 1.4954 |
| (I-327) | t-C$_4$H$_9$—C$_6$H$_4$—O—CH$_2$—C(CH$_3$)$_2$— | morpholino | 1.4962 |
| (I-328) | t-C$_4$H$_9$—C$_6$H$_4$—O—CH$_2$—C(CH$_3$)$_2$— | 4-methylpiperazino | 1.4975 |
| (I-329) | 2-OCH$_3$-C$_6$H$_4$—O—CH$_2$—C(CH$_3$)$_2$— | —N(n-C$_4$H$_9$)$_2$ | 1.5063 |
| (I-330) | 2-OCH$_3$-C$_6$H$_4$—O—CH$_2$—C(CH$_3$)$_2$— | pyrrolidino | 1.5057 |
| (I-331) | 2-OCH$_3$-C$_6$H$_4$—O—CH$_2$—C(CH$_3$)$_2$— | piperidino | 1.5070 |
| (I-332) | 2-OCH$_3$-C$_6$H$_4$—O—CH$_2$—C(CH$_3$)$_2$— | morpholino | 1.5067 |
| (I-333) | 2-OCH$_3$-C$_6$H$_4$—O—CH$_2$—C(CH$_3$)$_2$— | 3,5-dimethylpiperidino | 1.4944 |

-continued

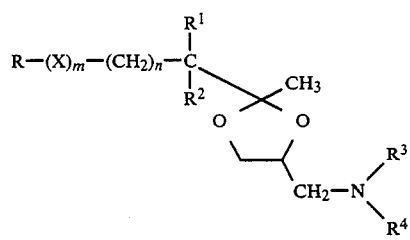

| Example No. | R—(X)$_m$—(CH$_2$)$_n$—C(R$^1$)(R$^2$) | —N(R$^3$)(R$^4$) | Physical constant [Refractive index n$_D^{20}$: melting point °C.] |
|---|---|---|---|
| (I-334) | 2-(i-C$_3$H$_7$O)C$_6$H$_4$—O—CH$_2$—C(CH$_3$)$_2$— | piperidino | 1.5087 |
| (I-335) | 2-(i-C$_3$H$_7$O)C$_6$H$_4$—O—CH$_2$—C(CH$_3$)$_2$— | morpholino | 1.5060 |
| (I-336) | 2-(i-C$_3$H$_7$O)C$_6$H$_4$—O—CH$_2$—C(CH$_3$)$_2$— | 4-methylpiperidino | 1.5095 |
| (I-337) | 2-(i-C$_3$H$_7$O)C$_6$H$_4$—O—CH$_2$—C(CH$_3$)$_2$— | 3,3-dimethylpiperidino | 1.5041 |
| (I-338) | 2,4-Cl$_2$C$_6$H$_3$—O—CH$_2$—C(CH$_3$)$_2$— | —N(CH$_3$)CH$_2$CH=C(CH$_3$)$_2$ | |
| (I-339) | 2,4-Cl$_2$C$_6$H$_3$—O—CH$_2$—C(CH$_3$)$_2$— | pyrrolidino | 1.5016 |
| (I-340) | 2,4-Cl$_2$C$_6$H$_3$—O—CH$_2$—C(CH$_3$)$_2$— | piperidino | 1.5006 |
| (I-341) | 2,4-Cl$_2$C$_6$H$_3$—O—CH$_2$—C(CH$_3$)$_2$— | hexamethyleneimino | 1.5076 |

-continued

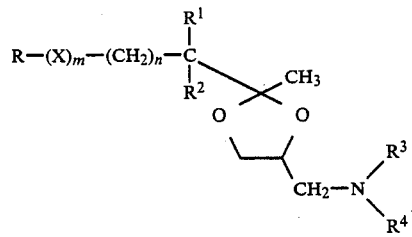
(Id)

| Example No. | R—(X)$_m$—(CH$_2$)$_n$—C(R$^1$)(R$^2$)— | —N(R$^3$)(R$^4$) | Physical constant [Refractive index n$_D^{20}$: melting point °C.] |
|---|---|---|---|
| (I-342) | 2,4-Cl$_2$C$_6$H$_3$—O—CH$_2$—C(CH$_3$)$_2$— | morpholino | 1.5064 |
| (I-343) | 2,4-Cl$_2$C$_6$H$_3$—O—CH$_2$—C(CH$_3$)$_2$— | 2-methylpiperidino | 1.4941 |
| (I-344) | 2,4-Cl$_2$C$_6$H$_3$—O—CH$_2$—C(CH$_3$)$_2$— | 3-methylpiperidino | 1.5034 |
| (I-345) | 2,4-Cl$_2$C$_6$H$_3$—O—CH$_2$—C(CH$_3$)$_2$— | 4-methylpiperidino | 1.4987 |
| (I-346) | 2,4-Cl$_2$C$_6$H$_3$—O—CH$_2$—C(CH$_3$)$_2$— | 4-methylpiperazino | 1.5023 |
| (I-347) | 2,4-Cl$_2$C$_6$H$_3$—O—CH$_2$—C(CH$_3$)$_2$— | 4-phenylpiperazino | 1.5092 |
| (I-348) | 2,4-Cl$_2$C$_6$H$_3$—O—CH$_2$—C(CH$_3$)$_2$— | 3,5-dimethylpiperidino | 1.4980 |
| (I-349) | 2,4-Cl$_2$C$_6$H$_3$—O—CH$_2$—C(CH$_3$)$_2$— | 2,4-dimethylpiperidino | 1.5021 |

-continued

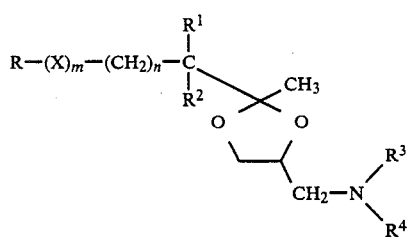
(Id)

| Example No. | R—(X)$_m$—(CH$_2$)$_n$—$\underset{R^2}{\overset{R^1}{C}}$— | —N$\underset{R^4}{\overset{R^3}{\diagdown}}$ | Physical constant [Refractive index n$_D^{20}$: melting point °C.] |
|---|---|---|---|
| (I-350) | 2,4-Cl$_2$C$_6$H$_3$—O—CH$_2$—C(CH$_3$)$_2$— | 2,6-dimethylpiperidino | 1.4980 |
| (I-351) | 2,4-(CH$_3$)$_2$C$_6$H$_3$—O—CH$_2$—C(CH$_3$)$_2$— | pyrrolidino | 1.5081 |
| (I-352) | 2,4-(CH$_3$)$_2$C$_6$H$_3$—O—CH$_2$—C(CH$_3$)$_2$— | piperidino | 1.5064 |
| (I-353) | 2,4-(CH$_3$)$_2$C$_6$H$_3$—O—CH$_2$—C(CH$_3$)$_2$— | 4-methylpiperazino | 1.5086 |
| (I-354) | 3,5-(CH$_3$)$_2$C$_6$H$_3$—O—CH$_2$—C(CH$_3$)$_2$— | piperidino | 1.4980 |
| (I-355) | 3,5-(CH$_3$)$_2$C$_6$H$_3$—O—CH$_2$—C(CH$_3$)$_2$— | hexamethyleneimino | 1.4941 |
| (I-356) | 3,5-(CH$_3$)$_2$C$_6$H$_3$—O—CH$_2$—C(CH$_3$)$_2$— | morpholino | 1.4979 |

-continued

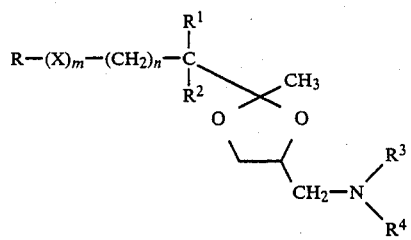
(Id)

| Example No. | R—(X)$_m$—(CH$_2$)$_n$—C(R$^1$)(R$^2$) | —N(R$^3$)(R$^4$) | Physical constant [Refractive index n$_D^{20}$: melting point °C.] |
|---|---|---|---|
| (I-357) | 3,5-dimethylphenyl-O-CH$_2$-C(CH$_3$)$_2$-CH$_3$ | 2-methylpiperidin-1-yl | 1.4953 |
| (I-358) | 3,5-dimethylphenyl-O-CH$_2$-C(CH$_3$)$_2$-CH$_3$ | 3-methylpiperidin-1-yl | 1.4939 |
| (I-359) | 3,5-dimethylphenyl-O-CH$_2$-C(CH$_3$)$_2$-CH$_3$ | 3,5-dimethylpiperidin-1-yl | 1.4902 |
| (I-360) | 3,5-dimethylphenyl-O-CH$_2$-C(CH$_3$)$_2$-CH$_3$ | 3,3-dimethylpiperidin-1-yl | 1.4900 |
| (I-361) | 3,5-dimethylphenyl-O-CH$_2$-C(CH$_3$)$_2$-CH$_3$ | 2,6-dimethylmorpholin-4-yl | 1.4905 |
| (I-362) | 2,4-dichlorophenyl-O-CH$_2$-C(CH$_3$)$_2$-CH$_3$ | 3,3-dimethylpiperidin-1-yl | 1.5044 |
| (I-363) | 2,4-dichlorophenyl-O-CH$_2$-C(CH$_3$)$_2$-CH$_3$ | 2,6-dimethylmorpholin-4-yl | 1.5034 |

-continued

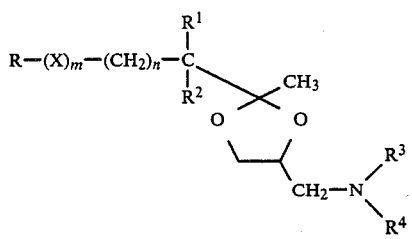
(Id)

| Example No. | R—(X)$_m$—(CH$_2$)$_n$—C(R$^1$)(R$^2$)— | —N(R$^3$)(R$^4$) | Physical constant [Refractive index n$_D^{20}$: melting point °C.] |
|---|---|---|---|
| (I-364) | 3,4-Cl$_2$-C$_6$H$_3$—O—CH$_2$—C(CH$_3$)$_2$— | hexamethyleneimino (azepan-1-yl) | 1.5128 |
| (I-365) | 3,4-Cl$_2$-C$_6$H$_3$—O—CH$_2$—C(CH$_3$)$_2$— | 3-methylpiperidin-1-yl | 1.5094 |
| (I-366) | 3,4-Cl$_2$-C$_6$H$_3$—O—CH$_2$—C(CH$_3$)$_2$— | 5-methyl-1,2,3,6-tetrahydropyridin-1-yl | 1.5039 |
| (I-367) | 3,4-Cl$_2$-C$_6$H$_3$—O—CH$_2$—C(CH$_3$)$_2$— | 4-methylpiperidin-1-yl | 1.5034 |
| (I-368) | 3,4-Cl$_2$-C$_6$H$_3$—O—CH$_2$—C(CH$_3$)$_2$— | 3,5-dimethylpiperidin-1-yl | 1.5087 |
| (I-369) | 3,4-Cl$_2$-C$_6$H$_3$—O—CH$_2$—C(CH$_3$)$_2$— | 2,6-dimethylmorpholin-4-yl | 1.5122 |
| (I-370) | 2,3-(CH$_3$)$_2$-C$_6$H$_3$—O—CH$_2$—C(CH$_3$)$_2$— | 3-methylpiperidin-1-yl | 1.5066 |

-continued

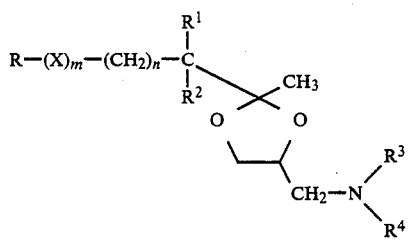
(Id)

| Example No. | R—(X)$_m$—(CH$_2$)$_n$—C(R$^1$)(R$^2$)— | —N(R$^3$)(R$^4$) | Physical constant [Refractive index n$_D^{20}$: melting point °C.] |
|---|---|---|---|
| (I-371) | 2,6-dimethylphenyl-O—CH$_2$—C(CH$_3$)$_2$— | pyrrolidin-1-yl | 1.5087 |
| (I-372) | 2,6-dimethylphenyl-O—CH$_2$—C(CH$_3$)$_2$— | piperidin-1-yl | 1.5074 |
| (I-373) | 2,6-dimethylphenyl-O—CH$_2$—C(CH$_3$)$_2$— | 4-methylpiperazin-1-yl | 1.5067 |
| (I-374) | 2,3,5-trimethylphenyl-O—CH$_2$—C(CH$_3$)$_2$— | morpholin-4-yl | 1.5034 |
| (I-375) | 2,3,5-trimethylphenyl-O—CH$_2$—C(CH$_3$)$_2$— | 4-methylpiperidin-1-yl | 1.5019 |
| (I-376) | 3-chloro-2-methylphenyl-O—CH$_2$—C(CH$_3$)$_2$— | hexamethyleneimin-1-yl | 1.5044 |
| (I-377) | 3-chloro-2-methylphenyl-O—CH$_2$—C(CH$_3$)$_2$— | 3-methylpiperidin-1-yl | 1.5052 |

-continued

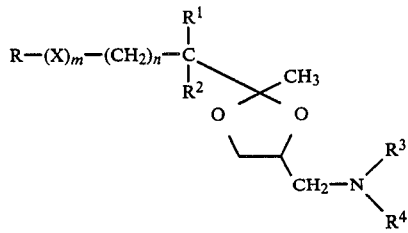
(Id)

| Example No. | R—(X)$_m$—(CH$_2$)$_n$—C(R$^1$)(R$^2$) | —N(R$^3$)(R$^4$) | Physical constant [Refractive index $n_D^{20}$: melting point °C.] |
|---|---|---|---|
| (I-378) | 3-Cl, 2-CH$_3$-phenyl-O-CH$_2$-C(CH$_3$)$_2$- | 3,3-dimethylpiperidino | 1.5042 |
| (I-379) | 3-Cl, 2-CH$_3$-phenyl-O-CH$_2$-C(CH$_3$)$_2$- | 3,5-dimethylpiperidino | 1.5039 |
| (I-380) | 3-Cl, 2-CH$_3$-phenyl-O-CH$_2$-C(CH$_3$)$_2$- | 2,6-dimethylmorpholino | 1.5067 |
| (I-381) | 4-Cl, 2-CH$_3$-phenyl-O-CH$_2$-C(CH$_3$)$_2$- | piperidino | 1.5038 |
| (I-382) | 4-Cl, 2-CH$_3$-phenyl-O-CH$_2$-C(CH$_3$)$_2$- | hexamethyleneimino | 1.5068 |
| (I-383) | 4-Cl, 2-CH$_3$-phenyl-O-CH$_2$-C(CH$_3$)$_2$- | 2-methylpiperidino | 1.5031 |
| (I-384) | 4-Cl, 2-CH$_3$-phenyl-O-CH$_2$-C(CH$_3$)$_2$- | 3-methylpiperidino | 1.5021 |
| (I-385) | 4-Cl, 2-CH$_3$-phenyl-O-CH$_2$-C(CH$_3$)$_2$- | 4-methylpiperidino | 1.5012 |

-continued

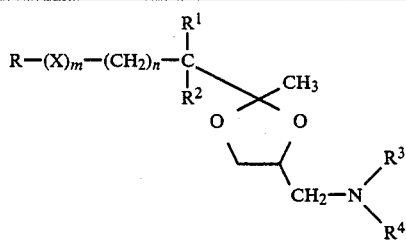
(Id)

| Example No. | R—(X)$_m$—(CH$_2$)$_n$—C(R$^1$)(R$^2$)— | —N(R$^3$)(R$^4$) | Physical constant [Refractive index n$_D^{20}$: melting point °C.] |
|---|---|---|---|
| (I-386) | 4-Cl, 2-CH$_3$-phenyl-O-CH$_2$-C(CH$_3$)$_2$- | 3,5-dimethylpiperidin-1-yl | 1.4984 |
| (I-387) | 4-Cl, 2-CH$_3$-phenyl-O-CH$_2$-C(CH$_3$)$_2$- | 3,3-dimethylpiperidin-1-yl | 1.5069 |
| (I-388) | 5-CH$_3$, 2-Cl-phenyl-O-CH$_2$-C(CH$_3$)$_2$- | hexamethyleneimin-1-yl | 1.5031 |
| (I-389) | 5-CH$_3$, 2-Cl-phenyl-O-CH$_2$-C(CH$_3$)$_2$- | 3-methylpiperidin-1-yl | 1.5004 |
| (I-390) | 5-CH$_3$, 2-Cl-phenyl-O-CH$_2$-C(CH$_3$)$_2$- | 3,3-dimethylpiperidin-1-yl | 1.5027 |
| (I-391) | 5-CH$_3$, 2-Cl-phenyl-O-CH$_2$-C(CH$_3$)$_2$- | 3,5-dimethylpiperidin-1-yl | 1.5017 |
| (I-392) | 5-CH$_3$, 2-Cl-phenyl-O-CH$_2$-C(CH$_3$)$_2$- | 2,6-dimethylmorpholin-4-yl | 1.5062/ boiling point: 198° C./0.5 mbar |

-continued

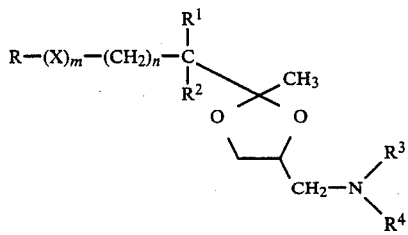

| Example No. | R—(X)$_m$—(CH$_2$)$_n$—C(R$^1$)(R$^2$) | —N(R$^3$)(R$^4$) | Physical constant [Refractive index n$_D^{20}$: melting point °C.] |
|---|---|---|---|
| (I-393) | 4-Cl, 2-C$_2$H$_5$-C$_6$H$_3$—O—CH$_2$—C(CH$_3$)$_2$— | azepan-1-yl | |
| (I-394) | 4-Cl, 2-C$_2$H$_5$-C$_6$H$_3$—O—CH$_2$—C(CH$_3$)$_2$— | 3-methylpiperidin-1-yl | |
| (I-395) | 4-Cl, 2-C$_2$H$_5$-C$_6$H$_3$—O—CH$_2$—C(CH$_3$)$_2$— | 3,5-dimethylpiperidin-1-yl | |
| (I-396) | 4-Cl-C$_6$H$_4$—S—C(CH$_3$)$_2$— | piperidin-1-yl | |
| (I-397) | 4-Cl-C$_6$H$_4$—S—C(CH$_3$)$_2$— | azepan-1-yl | 1.5061 |
| (I-398) | 4-Cl-C$_6$H$_4$—S—C(CH$_3$)$_2$— | 3-methylpiperidin-1-yl | 1.5067 |
| (I-399) | 4-Cl-C$_6$H$_4$—S—C(CH$_3$)$_2$— | 3,5-dimethylpiperidin-1-yl | 1.5044 |
| (I-400) | 4-Cl-C$_6$H$_4$—S—C(CH$_3$)$_2$— | 3,3-dimethylpiperidin-1-yl | |

-continued

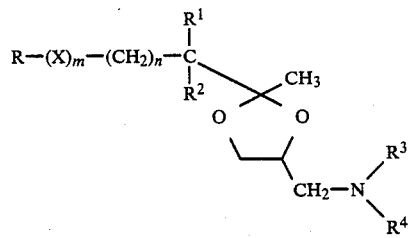
(Id)

| Example No. | R—(X)$_m$—(CH$_2$)$_n$—C(R$^1$)(R$^2$) | —N(R$^3$)(R$^4$) | Physical constant [Refractive index n$_D^{20}$: melting point °C.] |
|---|---|---|---|
| (I-401) | 4-Cl-C$_6$H$_4$—S—C(CH$_3$)$_2$— | 2,6-dimethylmorpholino | |
| (I-402) | C$_6$H$_5$—S—CH$_2$—C(CH$_3$)$_2$— | piperidino | 1.5445 |
| (I-403) | 2-Cl-C$_6$H$_4$—S—CH$_2$—C(CH$_3$)$_2$— | piperidino | 1.5422 |
| (I-404) | 4-Cl-C$_6$H$_4$—S—CH$_2$—C(CH$_3$)$_2$— | pyrrolidino | 1.5538 |
| (I-405) | 4-Cl-C$_6$H$_4$—S—CH$_2$—C(CH$_3$)$_2$— | piperidino | 1.5491 |
| (I-406) | 2,4-(CH$_3$)$_2$-C$_6$H$_3$—S—CH$_2$—C(CH$_3$)$_2$— | piperidino | 1.5457 |
| (I-407) | 4-Cl-C$_6$H$_4$—CH$_2$—CH(CH$_3$)— | 3-methylpiperidino | 1.5173 |
| (I-408) | 4-Cl-C$_6$H$_4$—CH$_2$—CH(CH$_3$)— | 4-phenylpiperidino | 1.5506 |
| (I-409) | 4-F-C$_6$H$_4$—O—CH$_2$—C(CH$_3$)$_2$— | 4-methylpiperazino | 1.4919 |

-continued

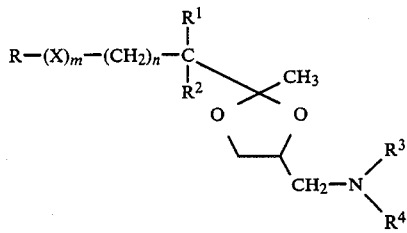

| Example No. | R—(X)$_m$—(CH$_2$)$_n$—C(R$^1$)(R$^2$)— | —NR$^3$R$^4$ | Physical constant [Refractive index n$_D^{20}$: melting point °C.] |
|---|---|---|---|
| (I-410) | ![structure] 2-ethylphenyl-O-C(CH$_3$)$_2$— | azepan-1-yl | |
| (I-411) | 4-Cl-C$_6$H$_4$-S-CH$_2$-C(CH$_3$)$_2$— | —N(CH$_3$)-CH$_2$-CH=C(CH$_3$)$_2$ | |

It will be understood that the specification and examples are illustrative but not limitative of the present invention and that other embodiments within the spirit and scope of the invention will suggest themselves to those skilled in the art.

We claim:

1. A fungicidal composition comprising a fungicidally effective amount of at least one amino compound selected from the group consisting of (I)

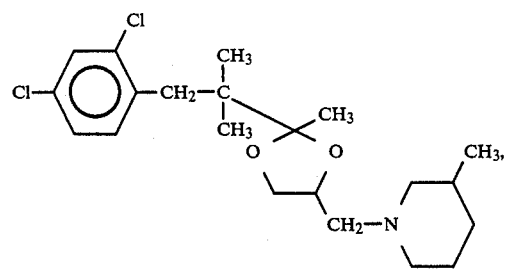
(I-140)

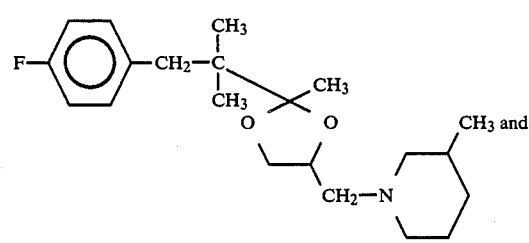
(I-89)

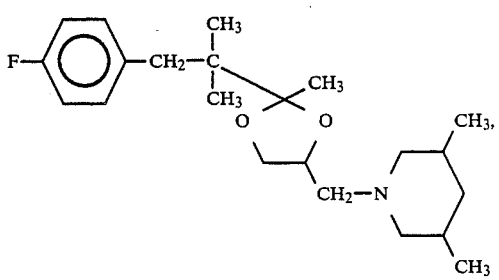
(I-92)

or an addition product thereof with an acid, metal salt or quaternizing agent, and (II) at least one compound selected from the group consisting of

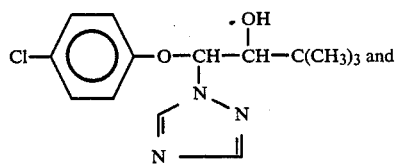
(IIb-2)

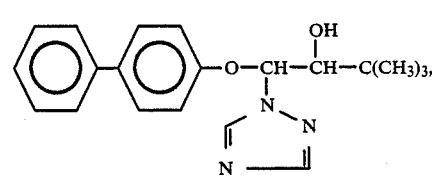
(IIb-3)

wherein the weight ratio of compound I to compound II is about 1:1.

2. A composition according to claim 1, wherein I is (I-140)
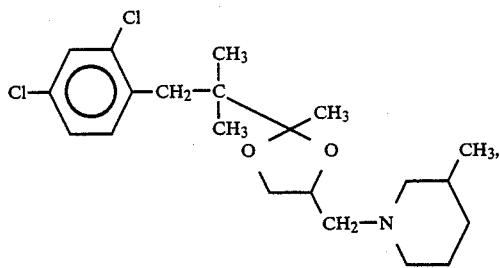

and II is (IIb-3)
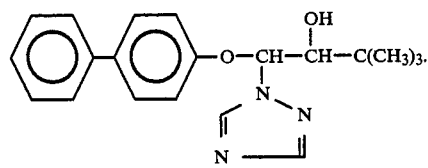

3. A composition according to claim 1, wherein I is (I-89)
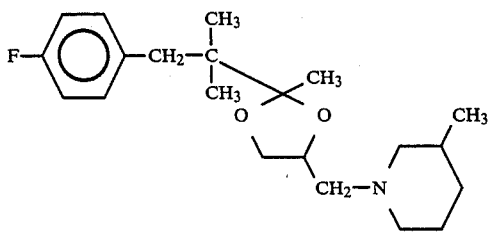

and II is (IIb-3)
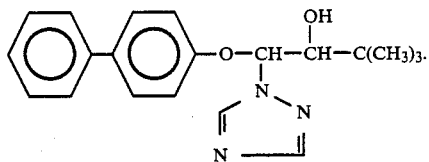

4. A composition according to claim 1, wherein I is (I-92)
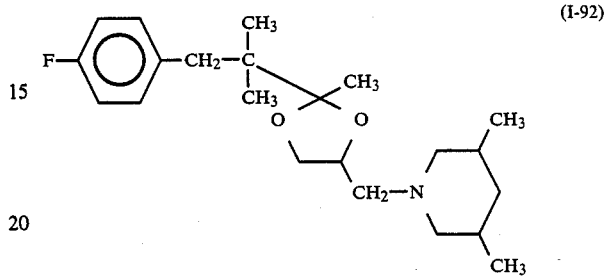

and II is (IIb-2)
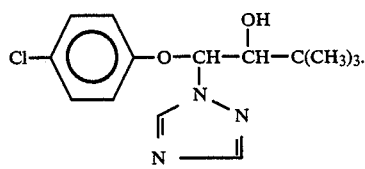

5. A method of combating fungi which comprises administering to such fungi or to a fungus habitat a fungicidally effective amount of a composition according to claim 1.

6. A method of combating fungi which comprises administering to such fungi or to a fungus habitat a fungicidally effective amount of a composition according to claim 2.

7. A method of combating fungi which comprises administering to such fungi or to a fungus habitat a fungicidally effective amount of a composition according to claim 3.

8. A method of combating fungi which comprises administering to such fungi or to a fungus habitat a fungicidally effective amount of a composition according to claim 4.

* * * * *

UNITED STATES PATENT AND TRADEMARK OFFICE
CERTIFICATE OF CORRECTION

PATENT NO. : 4,826,857  Page 1 of 2

DATED : May 2, 1989

INVENTOR(S) : Wolfgang Krämer, et al

It is certified that error appears in the above-identified patent and that said Letters Patent is hereby corrected as shown below:

| | |
|---|---|
| Title Page, "Inventors" line 2 | Correct --Weissmüller-- |
| Col. 5, line 4 | Delete "z" and substitute --Z-- |
| Col. 6, line 48 | Before "5" delete "as" and substitute --has-- |
| Col. 13, line 37 | Beginning of formula delete "$(CH_3)_3-$" and substitute --$(CH_3)_3C-$ -- |
| Col. 21, line 62 | Delete "piperidine" and substitute --piperidin-- |
| Col. 46, Example (I-79), 3rd column | Delete "1.5108" |
| Col. 46, Example (I-79), 4th column | Insert --1.5108-- |
| Col. 84, Example (I-221), last column | Delete "0.1 mbar" and substitute --0.2 mbar-- |
| Col. 86, (Example (I-228), 3rd column | Delete formula and substitute 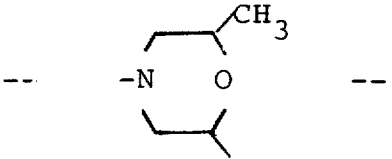 |
| Col. 90, Example (I-244) 4th column | Delete "1,4939" and substitute --1.4939-- |
| Col. 90, Example (I-246), 3rd column | Delete formula and substitute |

UNITED STATES PATENT AND TRADEMARK OFFICE
CERTIFICATE OF CORRECTION

PATENT NO. : 4,826,857

DATED : May 2, 1989

INVENTOR(S) : Wolfgang Krämer, et al

It is certified that error appears in the above-identified patent and that said Letters Patent is hereby corrected as shown below:

Col. 115, Examples (I-354), (I-355), (I-356); Col. 116, Examples (I-357), (I-358), (I-359), (I-360), and (I-361) second column of each Delete beginning of formula and substitute

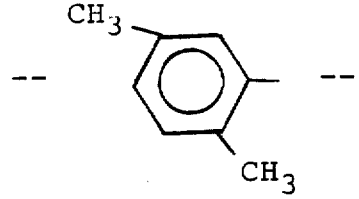

Signed and Sealed this

Fifteenth Day of May, 1990

Attest:

HARRY F. MANBECK, JR.

Attesting Officer

Commissioner of Patents and Trademarks